US012708379B2

(12) United States Patent
Kubacki et al.

(10) Patent No.: US 12,708,379 B2
(45) Date of Patent: Aug. 18, 2026

(54) SURGICAL GUIDES AND METHODS OF USING THE SAME

(71) Applicant: Wright Medical Technology, Inc., Memphis, TN (US)

(72) Inventors: Meghan R. Kubacki, Cookeville, TN (US); David R. Tuttle, Memphis, TN (US); Steven L. Haddad, Glenview, IL (US)

(73) Assignee: Wright Medical Technology, Inc., Memphis, TN (US)

( * ) Notice: Subject to any disclaimer, the term of this patent is extended or adjusted under 35 U.S.C. 154(b) by 919 days.

(21) Appl. No.: 18/054,948

(22) Filed: Nov. 14, 2022

(65) Prior Publication Data

US 2023/0270456 A1 Aug. 31, 2023

Related U.S. Application Data

(60) Provisional application No. 63/268,615, filed on Feb. 28, 2022.

(51) Int. Cl.

| | |
|---|---|
| ***A61B 17/17*** | (2006.01) |
| ***A61F 2/30*** | (2006.01) |
| ***A61F 2/42*** | (2006.01) |

(52) U.S. Cl.

CPC ........ *A61B 17/1775* (2016.11); *A61F 2/4202* (2013.01); *A61F 2002/30108* (2013.01); *A61F 2002/30891* (2013.01)

(58) Field of Classification Search

CPC .................................................. A61B 17/1775

See application file for complete search history.

(56) References Cited

U.S. PATENT DOCUMENTS

| | | | |
|---|---|---|---|
| 3,839,742 | A | 10/1974 | Link |
| 3,872,519 | A | 3/1975 | Giannestras et al. |
| 3,886,599 | A | 6/1975 | Schlein |
| 3,889,300 | A | 6/1975 | Smith |
| 3,896,502 | A | 7/1975 | Lennox |
| 3,896,503 | A | 7/1975 | Freeman et al. |
| 3,975,778 | A | 8/1976 | Newton, III |
| 3,987,500 | A | 10/1976 | Schlein |
| 4,021,864 | A | 5/1977 | Waugh |
| 4,069,518 | A | 1/1978 | Groth, Jr. et al. |

(Continued)

FOREIGN PATENT DOCUMENTS

| | | |
|---|---|---|
| CA | 2836651 | 3/2016 |
| CN | 101790353 | 7/2010 |

(Continued)

OTHER PUBLICATIONS

Search report issued for European U.S. Appl. No. 13/198,280 dated Feb. 5, 2014.

(Continued)

*Primary Examiner* — Nicholas W Woodall

(74) *Attorney, Agent, or Firm* — DUANE MORRIS LLP

(57) ABSTRACT

A surgical guide includes a body having a shape that corresponds to a shape of an implant to be implanted. The body defines a first opening and at least one hole that is sized and configured to receive a tool. A first alignment feature configured to facilitate alignment of the surgical guide with a first anatomic plane is coupled to the body. Systems and methods also are disclosed.

27 Claims, 15 Drawing Sheets

(56) References Cited

U.S. PATENT DOCUMENTS

| | | | |
|---|---|---|---|
| 4,156,944 | A | 6/1979 | Schreiber et al. |
| 4,166,292 | A | 9/1979 | Bokros |
| 4,204,284 | A | 5/1980 | Koeneman |
| 4,232,404 | A | 11/1980 | Samuelson et al. |
| 4,309,778 | A | 1/1982 | Buechel et al. |
| 4,470,158 | A | 9/1984 | Pappas et al. |
| 4,755,185 | A | 7/1988 | Tarr |
| 4,968,316 | A | 11/1990 | Hergenroeder |
| 5,041,139 | A | 8/1991 | Brånemark |
| 5,312,412 | A | 5/1994 | Whipple |
| 5,326,365 | A | 7/1994 | Alvine |
| 5,354,300 | A | 10/1994 | Goble et al. |
| 5,423,825 | A | 6/1995 | Levine |
| 5,476,466 | A | 12/1995 | Barrette et al. |
| 5,601,563 | A | 2/1997 | Burke et al. |
| 5,628,749 | A | 5/1997 | Vendrely et al. |
| 5,634,927 | A | 6/1997 | Houston et al. |
| 5,667,511 | A | 9/1997 | Vendrely et al. |
| 5,674,223 | A | 10/1997 | Cipolletti et al. |
| 5,735,904 | A | 4/1998 | Pappas |
| 5,766,259 | A | 6/1998 | Sammarco |
| 5,776,200 | A | 7/1998 | Johnson et al. |
| 5,817,097 | A | 10/1998 | Howard et al. |
| 5,824,106 | A | 10/1998 | Fournal |
| 5,879,389 | A | 3/1999 | Koshino |
| 5,885,299 | A | 3/1999 | Winslow et al. |
| 5,888,203 | A | 3/1999 | Goldberg |
| 5,897,559 | A | 4/1999 | Masini |
| 5,935,132 | A | 8/1999 | Bettuchi et al. |
| 6,002,859 | A | 12/1999 | DiGioia et al. |
| 6,033,405 | A | 3/2000 | Winslow et al. |
| 6,102,952 | A | 8/2000 | Koshino |
| 6,183,519 | B1 | 2/2001 | Bonnin et al. |
| 6,245,109 | B1 | 6/2001 | Mendes et al. |
| 6,342,056 | B1 | 1/2002 | Mac-Thiong et al. |
| 6,344,043 | B1 | 2/2002 | Pappas |
| 6,409,767 | B1 | 6/2002 | Pericéet al. |
| 6,436,146 | B1 | 8/2002 | Hassler et al. |
| 6,478,800 | B1 | 11/2002 | Fraser et al. |
| 6,520,964 | B2 | 2/2003 | Tallarida et al. |
| 6,530,930 | B1 | 3/2003 | Marino et al. |
| 6,602,259 | B1 | 8/2003 | Masini |
| 6,610,067 | B2 | 8/2003 | Tallarida et al. |
| 6,610,095 | B1 | 8/2003 | Pope et al. |
| 6,620,168 | B1 | 9/2003 | Lombardo et al. |
| 6,645,215 | B1 | 11/2003 | McGovern et al. |
| 6,663,669 | B1 | 12/2003 | Reiley |
| 6,673,116 | B2 | 1/2004 | Reiley |
| 6,679,917 | B2 | 1/2004 | Ek |
| 6,719,799 | B1 | 4/2004 | Kropf |
| 6,824,567 | B2 | 11/2004 | Tornier et al. |
| 6,852,130 | B2 | 2/2005 | Keller et al. |
| 6,860,902 | B2 | 3/2005 | Reiley |
| 6,863,691 | B2 | 3/2005 | Short et al. |
| 6,875,222 | B2 | 4/2005 | Long et al. |
| 6,875,236 | B2 | 4/2005 | Reiley |
| 6,926,739 | B1 | 8/2005 | O'Connor et al. |
| 6,939,380 | B2 | 9/2005 | Guzman |
| 6,942,670 | B2 | 9/2005 | Heldreth et al. |
| 7,001,394 | B2 | 2/2006 | Gundlapalli et al. |
| 7,011,687 | B2 | 3/2006 | Deffenbaugh et al. |
| 7,025,790 | B2 | 4/2006 | Parks et al. |
| 7,163,541 | B2 | 1/2007 | Ek |
| 7,210,933 | B2 * | 5/2007 | Haessler .............. A61C 8/0089 433/174 |
| 7,238,190 | B2 | 7/2007 | Schon et al. |
| 7,252,684 | B2 | 8/2007 | Dearnaley |
| 7,314,488 | B2 | 1/2008 | Reiley |
| 7,323,012 | B1 | 1/2008 | Stone et al. |
| 7,476,227 | B2 | 1/2009 | Tornier et al. |
| 7,481,814 | B1 | 1/2009 | Metzger |
| 7,485,147 | B2 | 2/2009 | Papps et al. |
| 7,534,246 | B2 | 5/2009 | Reiley et al. |
| 7,534,270 | B2 | 5/2009 | Ball |
| 7,615,082 | B2 | 11/2009 | Naegerl et al. |
| 7,618,421 | B2 | 11/2009 | Axelson, Jr. et al. |
| 7,625,409 | B2 | 12/2009 | Saltzman et al. |
| 7,641,697 | B2 | 1/2010 | Reiley |
| 7,678,151 | B2 | 3/2010 | Ek |
| 7,713,305 | B2 | 5/2010 | Ek |
| 7,717,920 | B2 | 5/2010 | Reiley |
| 7,763,080 | B2 | 7/2010 | Southworth |
| 7,803,158 | B2 | 9/2010 | Hayden |
| 7,850,698 | B2 | 12/2010 | Straszheim-Morley et al. |
| 7,896,883 | B2 | 3/2011 | Ek et al. |
| 7,896,885 | B2 | 3/2011 | Miniaci et al. |
| 7,909,882 | B2 | 3/2011 | Stinnette |
| 7,914,533 | B2 | 3/2011 | Nelson et al. |
| 7,963,996 | B2 | 6/2011 | Saltzman et al. |
| 8,002,841 | B2 | 8/2011 | Hasselman |
| 8,012,217 | B2 | 9/2011 | Strzepa et al. |
| 8,034,114 | B2 | 10/2011 | Reiley |
| 8,034,115 | B2 | 10/2011 | Reiley |
| 8,048,164 | B2 | 11/2011 | Reiley |
| 8,110,006 | B2 | 2/2012 | Reiley |
| 8,114,091 | B2 | 2/2012 | Ratron et al. |
| 8,128,627 | B2 | 3/2012 | Justin et al. |
| 8,167,888 | B2 | 5/2012 | Steffensmeier |
| 8,172,850 | B2 | 5/2012 | McMinn |
| 8,177,841 | B2 | 5/2012 | Ek |
| 8,268,007 | B2 | 9/2012 | Barsoum et al. |
| 8,303,667 | B2 | 11/2012 | Younger |
| 8,313,492 | B2 | 11/2012 | Wong et al. |
| 8,317,797 | B2 | 11/2012 | Rasmussen |
| 8,323,346 | B2 | 12/2012 | Tepic |
| 8,337,503 | B2 | 12/2012 | Lian |
| 8,361,159 | B2 | 1/2013 | Ek |
| 8,430,879 | B2 | 4/2013 | Stoneburner et al. |
| 8,475,463 | B2 | 7/2013 | Lian |
| 8,491,596 | B2 | 7/2013 | Long et al. |
| 8,579,980 | B2 | 11/2013 | DeLurio et al. |
| 8,715,362 | B2 | 5/2014 | Reiley et al. |
| 8,808,303 | B2 | 8/2014 | Stemniski et al. |
| 8,911,444 | B2 | 12/2014 | Bailey |
| 9,259,250 | B2 | 2/2016 | Saravia et al. |
| 9,480,571 | B2 | 11/2016 | McGinley et al. |
| 9,492,281 | B2 | 11/2016 | Rouyer et al. |
| 9,629,726 | B2 | 4/2017 | Reiley et al. |
| 9,629,730 | B2 | 4/2017 | Reiley |
| 9,907,561 | B2 | 3/2018 | Luna et al. |
| 10,034,678 | B2 | 7/2018 | Park et al. |
| 10,039,558 | B2 | 8/2018 | Park et al. |
| 10,136,904 | B2 | 11/2018 | McGinley et al. |
| 10,149,687 | B2 | 12/2018 | McGinley et al. |
| 10,182,832 | B1 | 1/2019 | Saltzman et al. |
| 10,206,688 | B2 | 2/2019 | Park et al. |
| 10,743,999 | B2 | 8/2020 | Reiley |
| 10,940,012 | B2 | 3/2021 | Sander et al. |
| 2002/0068977 | A1 | 6/2002 | Jackson |
| 2002/0082607 | A1 | 6/2002 | Heldreth et al. |
| 2002/0133164 | A1 | 9/2002 | Williamson |
| 2002/0173853 | A1 | 11/2002 | Corl et al. |
| 2003/0208280 | A1 | 11/2003 | Tohidi |
| 2003/0236522 | A1 | 12/2003 | Long et al. |
| 2004/0030399 | A1 | 2/2004 | Asencio |
| 2004/0039394 | A1 | 2/2004 | Conti et al. |
| 2004/0068322 | A1 | 4/2004 | Ferree |
| 2004/0167631 | A1 | 8/2004 | Luchesi et al. |
| 2004/0186585 | A1 | 9/2004 | Feiwell |
| 2004/0193268 | A1 | 9/2004 | Hazebrouck |
| 2004/0216259 | A1 | 11/2004 | Ponziani |
| 2004/0236431 | A1 | 11/2004 | Sekel |
| 2005/0004676 | A1 | 1/2005 | Schon et al. |
| 2005/0165408 | A1 | 7/2005 | Puno et al. |
| 2005/0192674 | A1 | 9/2005 | Ferree |
| 2006/0009857 | A1 | 1/2006 | Gibbs et al. |
| 2006/0020345 | A1 | 1/2006 | O'Connor et al. |
| 2006/0036257 | A1 | 2/2006 | Steffensmeier |
| 2006/0116679 | A1 | 6/2006 | Lutz et al. |
| 2006/0142870 | A1 | 6/2006 | Robinson et al. |
| 2006/0235541 | A1 | 10/2006 | Hodorek |
| 2006/0247788 | A1 | 11/2006 | Ross |
| 2007/0038303 | A1 | 2/2007 | Myerson et al. |
| 2007/0100346 | A1 | 5/2007 | Wyss et al. |

(56) References Cited

U.S. PATENT DOCUMENTS

| | | | |
|---|---|---|---|
| 2007/0112431 A1 | 5/2007 | Kofoed | |
| 2007/0162025 A1 | 7/2007 | Tornier et al. | |
| 2007/0173944 A1 | 7/2007 | Keller et al. | |
| 2007/0173947 A1 | 7/2007 | Ratron | |
| 2007/0213830 A1 | 9/2007 | Ammann et al. | |
| 2007/0233129 A1 | 10/2007 | Bertagnoli et al. | |
| 2007/0276400 A1 | 11/2007 | Moore et al. | |
| 2007/0288030 A1 | 12/2007 | Metzger et al. | |
| 2008/0015602 A1 | 1/2008 | Axelson | |
| 2008/0097617 A1 | 4/2008 | Fellinger et al. | |
| 2008/0103603 A1 | 5/2008 | Hintermann | |
| 2008/0109081 A1 | 5/2008 | Bao et al. | |
| 2008/0195233 A1 | 8/2008 | Ferrari et al. | |
| 2008/0215156 A1 | 9/2008 | Duggal et al. | |
| 2008/0287954 A1 | 11/2008 | Kunz et al. | |
| 2008/0312745 A1 | 12/2008 | Keller et al. | |
| 2009/0024131 A1 | 1/2009 | Metzger et al. | |
| 2009/0043309 A1 | 2/2009 | Rasmussen | |
| 2009/0043310 A1 | 2/2009 | Rasmussen | |
| 2009/0054992 A1 | 2/2009 | Landes et al. | |
| 2009/0082875 A1 | 3/2009 | Long | |
| 2009/0105767 A1 | 4/2009 | Reiley | |
| 2009/0105840 A1 | 4/2009 | Reiley | |
| 2009/0182433 A1 | 7/2009 | Reiley et al. | |
| 2009/0198341 A1 | 8/2009 | Choi et al. | |
| 2009/0234360 A1 | 9/2009 | Alexander | |
| 2009/0276052 A1 | 11/2009 | Regala et al. | |
| 2010/0010493 A1 | 1/2010 | Dower | |
| 2010/0023066 A1 | 1/2010 | Long et al. | |
| 2010/0023126 A1 | 1/2010 | Grotz | |
| 2010/0057216 A1 | 3/2010 | Gannoe et al. | |
| 2010/0069910 A1 | 3/2010 | Hasselman | |
| 2010/0198355 A1 | 8/2010 | Kofoed et al. | |
| 2010/0212138 A1 | 8/2010 | Carroll et al. | |
| 2010/0241237 A1 | 9/2010 | Pappas | |
| 2010/0305572 A1 | 12/2010 | Saltzman et al. | |
| 2010/0318088 A1 | 12/2010 | Warne et al. | |
| 2010/0331984 A1 | 12/2010 | Barsoum et al. | |
| 2011/0029090 A1 | 2/2011 | Zannis et al. | |
| 2011/0035018 A1 | 2/2011 | Deffenbaugh et al. | |
| 2011/0035019 A1 | 2/2011 | Goswami et al. | |
| 2011/0071645 A1 | 3/2011 | Bojarski et al. | |
| 2011/0106268 A1 | 5/2011 | Deffenbaugh et al. | |
| 2011/0112542 A1 | 5/2011 | Gross | |
| 2011/0125200 A1 | 5/2011 | Hanson et al. | |
| 2011/0125275 A1 | 5/2011 | Lipman et al. | |
| 2011/0125284 A1 | 5/2011 | Gabbrielli et al. | |
| 2011/0152868 A1 | 6/2011 | Kourtis et al. | |
| 2011/0152869 A1 | 6/2011 | Ek et al. | |
| 2011/0166608 A1 | 7/2011 | Duggal et al. | |
| 2011/0190829 A1 | 8/2011 | Duggal et al. | |
| 2011/0218542 A1 | 9/2011 | Lian | |
| 2011/0245835 A1 | 10/2011 | Dodd et al. | |
| 2011/0253151 A1 | 10/2011 | Tochigi et al. | |
| 2011/0276052 A1 | 11/2011 | Hasselman | |
| 2011/0295380 A1 | 12/2011 | Long | |
| 2012/0010718 A1 | 1/2012 | Still | |
| 2012/0046753 A1 | 2/2012 | Cook et al. | |
| 2012/0053591 A1 | 3/2012 | Haines et al. | |
| 2012/0053644 A1 | 3/2012 | Landry et al. | |
| 2012/0083789 A1 | 4/2012 | Blakemore et al. | |
| 2012/0109131 A1 | 5/2012 | Vasarhelyi et al. | |
| 2012/0109326 A1 | 5/2012 | Perler | |
| 2012/0130376 A1 | 5/2012 | Loring et al. | |
| 2012/0130434 A1* | 5/2012 | Stemniski | A61B 17/1775 606/86 R |
| 2012/0136443 A1 | 5/2012 | Wenzel | |
| 2012/0185057 A1 | 7/2012 | Abidi et al. | |
| 2012/0191210 A1 | 7/2012 | Ratron et al. | |
| 2012/0239045 A1 | 9/2012 | Li | |
| 2012/0245701 A1 | 9/2012 | Zak et al. | |
| 2012/0271430 A1 | 10/2012 | Arnett et al. | |
| 2012/0277745 A1 | 11/2012 | Lizee | |
| 2013/0041473 A1 | 2/2013 | Rouyer et al. | |
| 2013/0116797 A1 | 5/2013 | Coulange et al. | |
| 2014/0276853 A1 | 9/2014 | Long et al. | |
| 2014/0309640 A1 | 10/2014 | Smith et al. | |
| 2015/0045801 A1 | 2/2015 | Axelson et al. | |
| 2016/0135815 A1 | 5/2016 | Loring et al. | |
| 2018/0177511 A1 | 6/2018 | Luna et al. | |
| 2018/0263639 A1 | 9/2018 | McGinley et al. | |
| 2019/0059917 A1 | 2/2019 | Saltzman | |
| 2019/0059918 A1 | 2/2019 | Saltzman et al. | |
| 2019/0133612 A1 | 5/2019 | McGinley | |
| 2021/0298770 A1* | 9/2021 | Allard | A61B 34/10 |
| 2021/0298771 A1* | 9/2021 | Lee | A61B 17/15 |
| 2021/0353313 A1* | 11/2021 | Lee | A61B 17/66 |
| 2022/0370081 A1* | 11/2022 | Moore | A61B 17/1739 |
| 2023/0263535 A1* | 8/2023 | Hyer | A61B 17/15 606/82 |
| 2023/0310012 A1* | 10/2023 | Reynolds | A61B 17/1775 606/86 R |
| 2024/0398489 A1* | 12/2024 | Stemniski | A61B 17/15 |
| 2025/0040939 A1* | 2/2025 | Lee | A61B 17/15 |

FOREIGN PATENT DOCUMENTS

| | | |
|---|---|---|
| EP | 2967697 | 4/2018 |
| EP | 2742877 B1 | 10/2019 |
| EP | 3354233 | 10/2019 |
| EP | 3878383 B1 | 8/2023 |
| GB | 2480846 | 12/2011 |
| JP | H11-500035 | 1/1999 |
| JP | 2006150055 | 6/2006 |
| JP | 2007518453 | 7/2007 |
| JP | 2007519477 | 7/2007 |
| JP | 2007536011 | 12/2007 |
| JP | 2011526189 | 10/2011 |
| JP | 2012518517 | 8/2012 |
| JP | 2013500810 | 1/2013 |
| JP | 2013511358 | 4/2013 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009143374 | 11/2009 |
| WO | WO 2009158522 | 12/2009 |
| WO | WO 2010099142 | 9/2010 |
| WO | WO 2010135156 | 11/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |
| WO | WO 2016039762 | 3/2016 |
| WO | 2019213122 A1 | 11/2019 |
| WO | 2020123295 A1 | 6/2020 |

OTHER PUBLICATIONS

International Search Report for International patent application No. PCT/US2014/027448 dated Jul. 7, 2014.

International Preliminary Report on Patentability issued for International patent application No. PCT/US2014/027448, Sep. 15, 2015, 8 pages.

Partial European Search Report issued in connection with European patent application No. 14768333.8, Oct. 26, 2016, 6 pages.

Patent Examination Report No. 1 issued in connection with Australian patent application No. 2015202080, Jul. 5, 2016, 4 pages.

First Office Action issued for Japanese patent application No. 2016-117842, Sep. 12, 2017, 5 pages.

First Office Action issued in connection with corresponding Japanese Patent Application No. 2020-016447, Apr. 6, 2021, 4 pages.

Office Action in corresponding Canadian Patent Application No. 2,904,652, Jun. 2, 2020, 6 pages.

First Examination Report issued in corresponding Australian Patent Application No. 2019213412, Sep. 3, 2020, 5 pages.

(56) References Cited

OTHER PUBLICATIONS

First Office Action in corresponding Canadian Patent Application No. 2,904,652, Jan. 28, 2020, 5 pages.
Final Office Action issued in connection with corresponding Japanese Patent Application No. 206-502443, May 15, 2018, 3 pages.
Extended European Search Report issued in connection with corresponding European Patent Application No. 18160378.8, Jun. 29, 2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, Sep. 3, 2018, 3 pages.
Examination Report No. 1 issued in connection with corresponding Australian Patent Application No. 20182000073, Dec. 24, 2018, 3 pages.
First Office Action issued in connection with corresponding Japanese Patent Application No. 2018-092289, Mar. 5, 2019, 2 pages.
Extended European Search Report and Opinion in connection with European Patent Application No. 14768333.8, dated Jan. 30, 2017, 10 pages.
First Office Action issued in connection with Chinese Patent Application No. 2017800899442 dated Apr. 6, 2022, 8 pages.
International Search Report and Written Opinion issued in connection with International Patent Application No. PCT/US2021/025873, Sep. 2, 2021.
Orthopedic Designs North America, Inc., http://odi-na.com/?service=talon-distalfix-fermoral-nail-system, accessed via Internet, Jul. 22, 2022.
Arthrex, "Arthrex—Intramedullary Nails," https://ww.arthrex.com/foot-ankle/intramedullary-nails, accessed via Internet, Jul. 22, 2022.
Inbone II Total Ankle Surgical Technique, Wright Medical Technology, Inc., Mar. 12, 2014, 64 pages.
Infinity Total Ankle System Surgical Technique, Wright Medical Techology, Inc., Aug. 8, 2015, 76 pages.
Partial European Search Report issued in connection with corresponding European Patent Application No. 22208047.5, Sep. 22, 2023, 9 pages.

* cited by examiner 206
210-2
208
210-1
202
204

218-4
218-3
218-2
218-1
206
212
210-2
214
210-1
208
202
216-4
216-3
216-2
216-1
204
200

208
202

SURGICAL GUIDES AND METHODS OF USING THE SAME

CROSS-REFERENCE TO RELATED APPLICATION

This application claims priority under 35 U.S.C. § 119(e) to U.S. Provisional Application No. 63/268,615, filed on Feb. 28, 2022, the entire contents of which are incorporated herein by reference.

INCORPORATION BY REFERENCE

The disclosures of U.S. Pat. Nos. 9,480,571 and 10,136,904 are incorporated by reference herein in their entireties.

FIELD OF DISCLOSURE

The disclosed apparatuses, systems, and methods relate to surgical tools. More specifically, the disclosed apparatuses, systems, and methods relate to surgical tools for performing ankle surgery, including total ankle surgery.

BACKGROUND

The ankle is a joint that acts much like a hinge. The joint is formed by the union of the three bones. The ankle bone is the talus. The top of the talus fits inside a socket that is formed by the lower leg, including the tibia and the fibula. Arthritis, bone degeneration, and/or injury can cause ankle joint deterioration resulting in pain, reduced range of motion, and decreased quality of life. In many cases, physicians recommend ankle replacement surgery with an implant. One example of such an implant is the INBONE™ Total Ankle System available from Stryker, of Memphis, TN, although one of ordinary skill in the art will understand that the disclosure is not limited to such implants. The process of implanting an ankle replacement system typically includes the use of sizing and/or cutting (e.g., drilling and/or resection) guides.

SUMMARY

The disclosed guides, systems, and methods provide enhanced durability and have a reduced size, which improves the ability of the surgeon to manipulate the guide during surgery. Further, the disclosed guides, systems, and methods provide enhanced visibility of the surface(s) to be cut during the surgery while reducing the number of components used compared to conventional instrumentation, which yields a more streamlined and efficient method.

As described above, in some embodiments, a surgical guide includes a body has a shape that corresponds to a shape of an implant. In some embodiments, an outer periphery of the body defines the shape that corresponds to the shape of the implant. The body defines an opening and at least one hole that is sized and configured to receive a tool therein. A first alignment feature may be coupled to the body. The first alignment feature is configured to facilitate alignment of the surgical guide with a first anatomic plane.

In some embodiments, the first opening is defined between a first side of the body, a second side of the body, a third side of the body, and a fourth side of the body.

In some embodiments, a second alignment feature extends from the second side of the body and is configured to facilitate alignment of the surgical guide with a second anatomic plane that is different from the first anatomic plane.

In some embodiments, first and second legs may extend from the first side of the body. Each of the first and second legs may define a respective hole that is sized and configured to receive a connection feature of another surgical guide.

In some embodiments, the connection feature includes a dowel.

In some embodiments, at least one of the first and second legs includes at least one step. The at least one step may provide a visual indication as to a location of a surface of a prosthesis to be implanted.

In some embodiments, the first and second legs include a plurality of steps.

In some embodiments, the first and second legs include a beveled surface.

In some embodiments, the first anatomic plane is a sagittal plane, and the second anatomic plane is a frontal plane.

In some embodiments, the first alignment feature includes a first component and a second component. The first component may include an opening, and the second component may include a projection that terminates in a shape that is complementary to a shape of the opening.

In some embodiments, the opening is defined by a block.

In some embodiments, the second alignment feature includes an opening and a projection that terminates in a shape that is complementary to a shape of the opening.

In some embodiments, the opening is defined by a block.

In some embodiments, the projection terminates from a flange that has a cross-sectional geometry to facilitate the coupling of the surgical guide to another surgical tool. In some embodiments the cross-sectional geometry has a trapezoidal shape.

In some embodiments, the at least one hole includes a first hole, a second hole, and a third hole disposed between the first hole and the second hole.

In some embodiments, the first hole is defined by a first bushing that extends from the body, the second hole is defined by a second bushing that extends from the body, and the third hole is defined by a third bushing that extends from the body.

In some embodiments, the body defines at least one slot that is disposed between the opening and the second side. The at least one slot may be sized and configured to receive a tool, including at least one of a depth indicating tool or a blade of a cutting tool.

In some embodiments, at least one of a posterior side or an anterior side of the body includes a notch configured to provide a visual indication of a location of at least one surface of a prosthesis to be implanted when the surgical guide is viewed in a sagittal plane.

In some embodiments, the body includes a joint line indicator.

In some embodiments, the joint line indicator includes at least one projection extending into the opening defined by the body.

In some embodiments, the joint line indicator includes a notch formed in at least one of a posterior side and/or an anterior side of the body.

In some embodiments, a first guide includes a first side, a second side, a third side, and a fourth side. The third and fourth sides extend between the first and second sides. The body defines a first opening between the first side, the second side, the third side, and the fourth side. The body may further define a first hole and a second hole each sized and configured to receive at least one fixation and/or and a cutting tool therein. A first alignment feature may extend from the second side of the body and be configured to facilitate alignment of the first guide with a first anatomic plane, and a second alignment feature may extend from the second side of the body and be configured to facilitate alignment of the first guide with a second anatomic plane. In some embodiments, the first anatomic plane and the second anatomic plane are the same. In some embodiments, the first anatomic plane and the second anatomic plane are different.

In some embodiments, the first guide includes first and second legs extending from the first side of the first guide body. A gap may be defined between the first leg, the second leg, and the first side of the first guide body.

In some embodiments, the system includes a second guide. The second guide may have a transverse beam that extends between a first arm and a second arm. The second guide may be configured to be coupled to the first guide.

In some embodiments, first and second protrusions extend from the transverse beam of the second guide. The first and second protrusions may be sized and configured to be received in respective connection features defined by the first and second legs of the first guide body for coupling the second guide to the first guide. In some embodiments, each connection feature includes a hole. In some embodiments, each connection feature includes a slot.

In some embodiments, each of the first and second arms of the second guide define at least one connection feature for receiving an elongate radiopaque device therein. In some embodiments, the at least one connection feature includes a hole. In some embodiments, the at least one connection feature includes a slot.

In some embodiments, the system includes a drill bit that extends from a first end to a second end. The first end may be configured to be coupled to a driving tool, and the second end may include at least one cutting surface. The drill bit may include at least one indicia located along its length at a distance from the second end. The distance of the at least one indicia from the second end may correspond to a length of an implant. The drill bit may be sized and configured to be received in a third hole defined by the first guide body.

In some embodiments, the third hole defined by the first guide body is located between the first hole and the second hole.

In some embodiments, the at least one indicia includes a plurality of indicia. Each indicia of the plurality of indicia may be disposed at a respective distance from the second end of the drill bit. The respective distance may correspond to a respective length of a different implant.

In some embodiments, a method includes coupling a first guide to an adjustment block, aligning a fluoroscope with the first guide in at least one anatomic plane using at least one of a first alignment feature and a second alignment feature of the first guide, and securing the first guide to a tibia once a desired alignment of the first guide has been achieved. In some embodiments, the second guide includes first and second arms that are coupled together a transverse beam.

In some embodiments, a method includes coupling a second guide to the first guide and coupling the second guide to the first guide includes inserting at least one protrusion extending from the transverse beam of the second guide into at least one connection feature of the first guide. In some embodiments, the at least one connection feature of the first guide includes at least one hole defined by the first guide. In some embodiments, the at least one connection feature of the first guide includes at least one slot defined by the first guide.

In some embodiments, a method includes determining a size of an implant to be implanted. The determining may be based at least in part on view of the first guide under fluoroscopy.

In some embodiments, determining the size of the implant includes inserting a drill bit into a hole defined by the first guide and into the tibia, and identifying an indicia disposed along a length of the drill bit.

In some embodiments, a method includes preparing a tibia for resection by inserting a drill into a first corner drill hole defined by the first guide.

In some embodiments, a method includes inserting the drill into a second corner drill hole defined by the first guide.

BRIEF DESCRIPTION OF THE DRAWINGS

These and other features and advantages of the apparatuses and methods described herein will be more fully disclosed in, or rendered obvious by, the following detailed description of the preferred embodiments, which is to be considered together with the accompanying drawings wherein like numbers refer to like parts.

DETAILED DESCRIPTION

Figure 1:
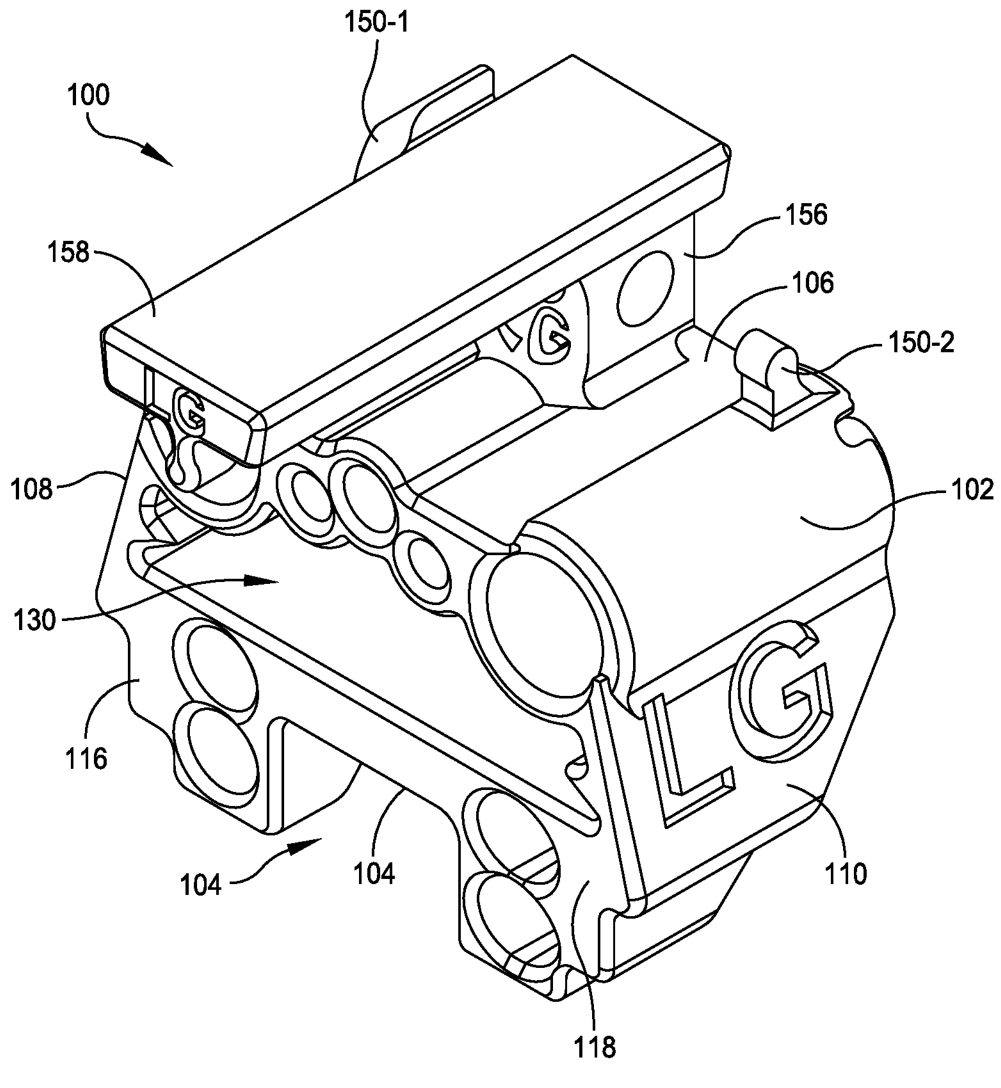
FIG. 1 is an isometric perspective view of one example of a guide in accordance with some embodiments.

This description of the exemplary embodiments is to be read in connection with the accompanying drawings, which are to be considered part of the entire written description.

The disclosed guides provide enhanced durability and have a reduced size, which improves the ability of the surgeon to manipulate the guide during surgery. Further, the disclosed guides provide enhanced visibility of the surface(s) to be cut during the surgery while reducing the number of components used compared to conventional instrumentation, which yields a more streamlined and efficient method.

In addition, this description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Figure 3:
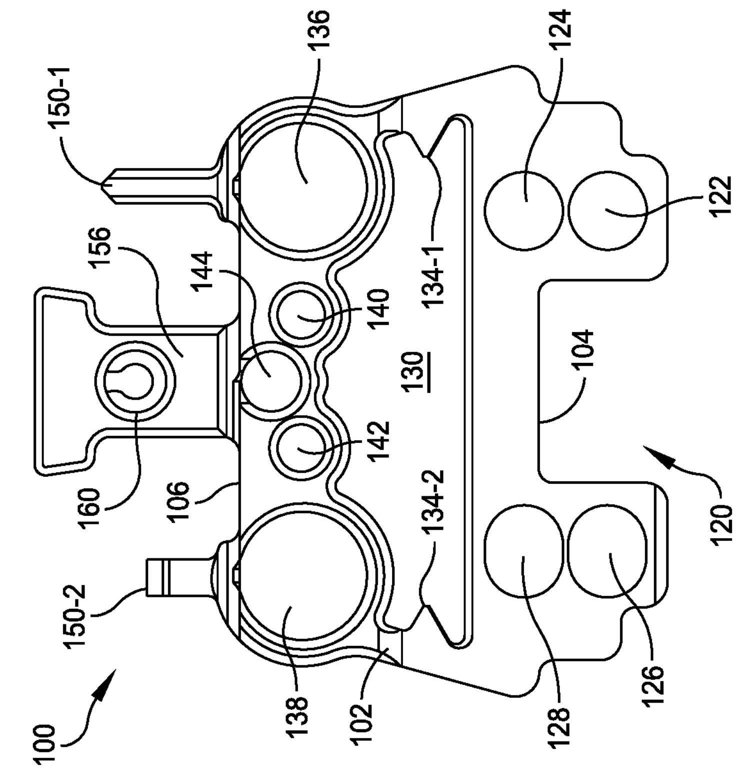
FIG. 3 is a rear or posterior side view of the guide illustrated in FIG. 1 in accordance with some embodiments.
Figure 2:
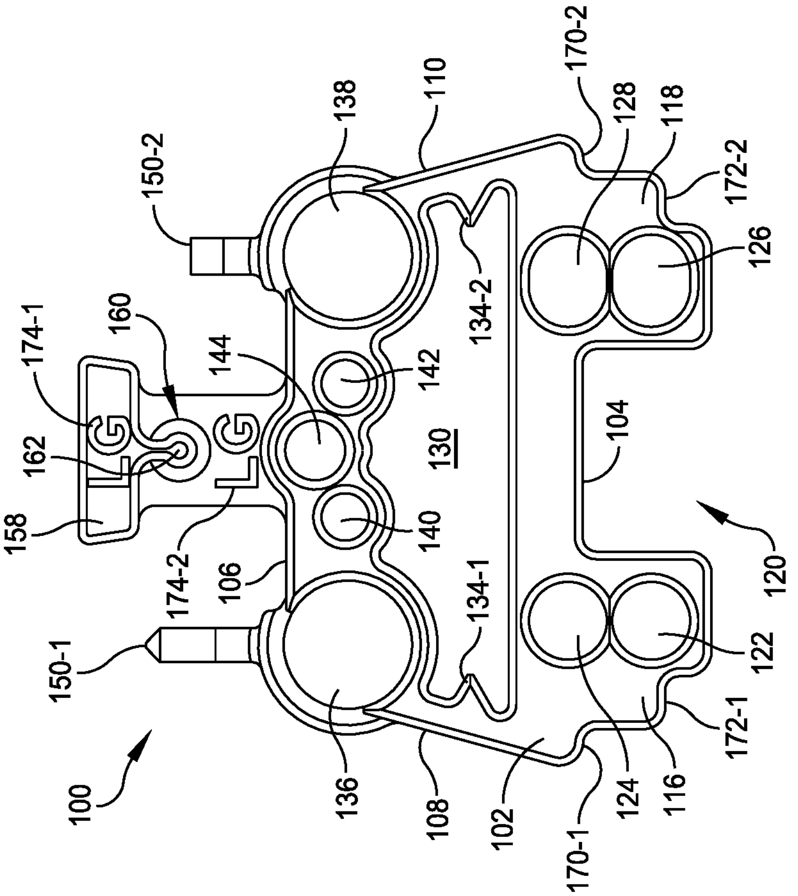
FIG. 2 is a front or anterior side view of the guide illustrated in FIG. 1 in accordance with some embodiments.
Figure 5:
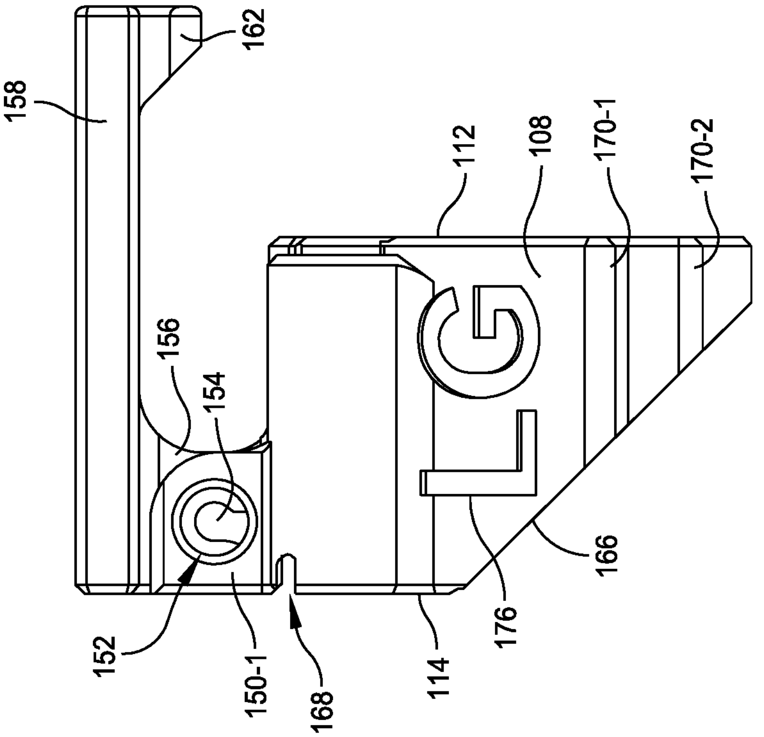
FIG. 5 is a side view of the guide illustrated in FIG. 1 that is opposite the side view of FIG. 4 in accordance with some embodiments.
Figure 4:
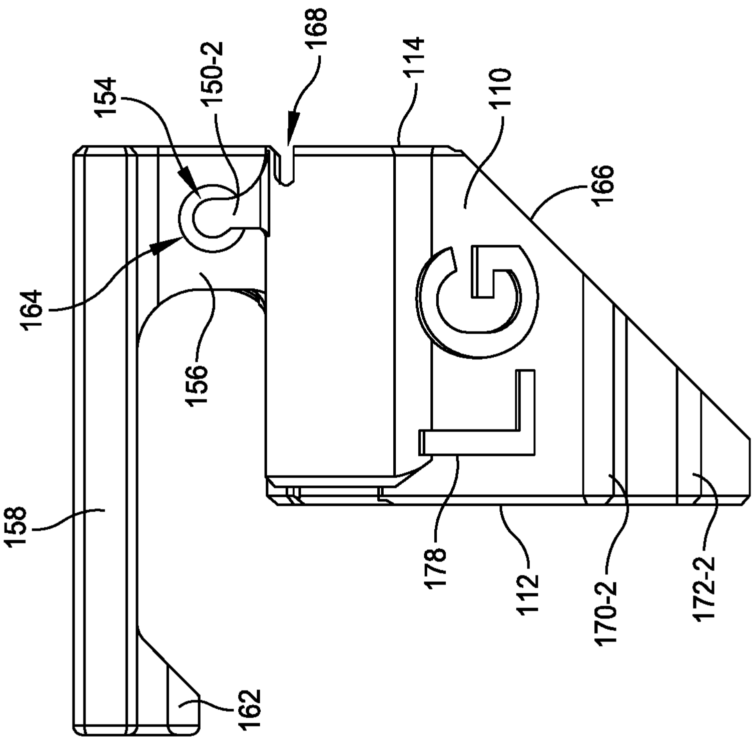
FIG. 4 is a side view of the guide illustrated in FIG. 1 in accordance with some embodiments.
Figure 7:
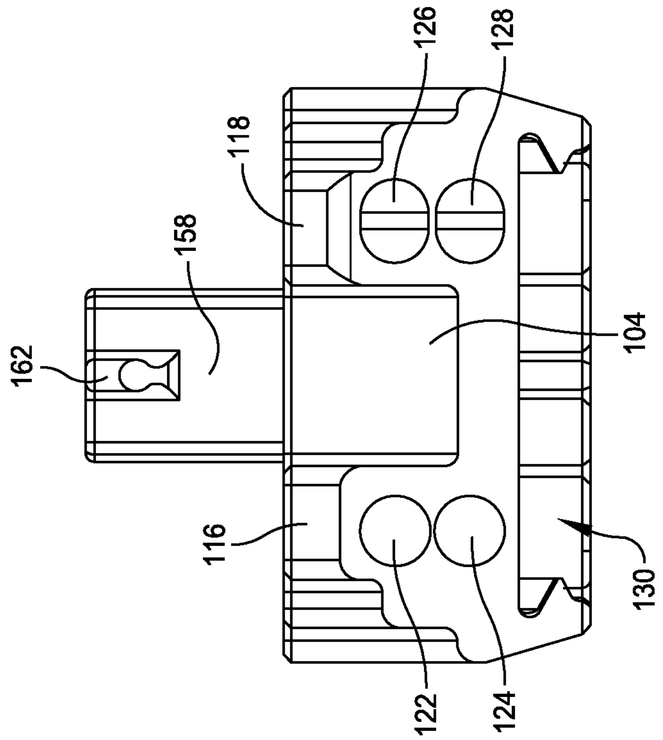
FIG. 7 is a bottom or inferior side view of the guide illustrated in FIG. 1 in accordance with some embodiments.
Figure 6:
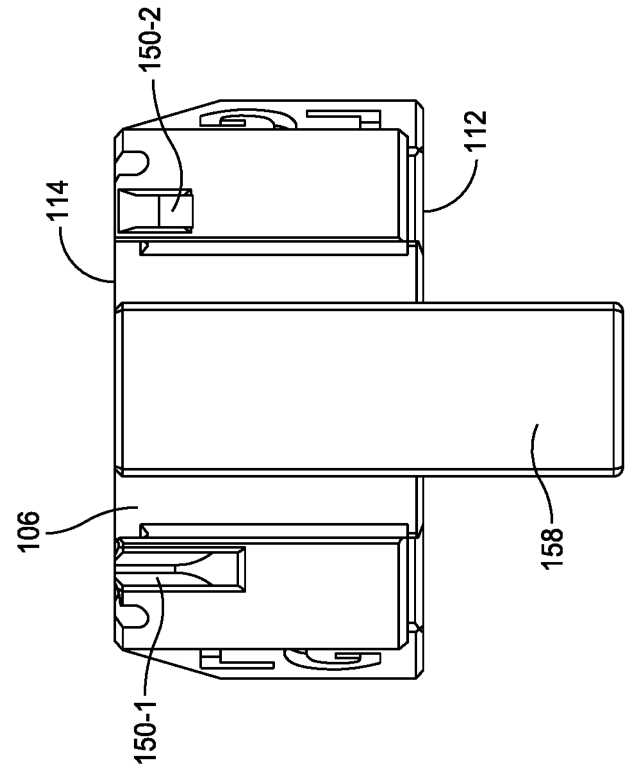
FIG. 6 is a top or superior side view of the guide illustrated in FIG. 1 in accordance with some embodiments.

FIGS. 1-7 illustrate one example of a combination sizing and drill guide 100 in accordance with some embodiments. Guide 100 includes a body 102 extending from an inferior side 104 to a superior side 106, as best seen in FIGS. 2 and 3. Body 102 further includes opposed sides 108, 110 (FIGS. 2 and 3), an anterior side 112, and a posterior side 114, as best seen in FIGS. 4 and 5. The profile of guide 100, such as defined by inferior side 104, superior side 106, and opposed sides 108, 110, which is shown has having a generally trapezoidal shape, may correspond to the profile of a prosthesis component. For example, the profile and/or outer periphery of guide 100 defined by inferior side 104, superior side 106, and opposed sides 108, 110 may correspond to the tibial and/or talar prosthesis components of a total ankle replacement system, although one of ordinary skill in the art will understand that body 102 of guide 100 may have a shape that corresponds to other types of implants.

In some embodiments, body 102 may be formed from a rigid radiopaque material, such as a surgical grade metal. One of ordinary skill in the art will understand that guide 100 may be formed from other materials, such as a combination of radiolucent (e.g., Radel® polyphenylsulfone (PPSU), available from Solvay) and radiopaque (e.g., stainless steel, aluminum, titanium, cobalt, chromium) materials. Guide 100 may be machined from a single block of material, molded, or formed using an additive manufacturing process (e.g., Direct Metal Laser Sintered (DMLS), Electron Beam Melting (EBM)).

The inferior side 104 may include a pair of spaced apart legs 116, 118 that extend inferiorly from body 102. A gap 120 is defined between the legs 116, 118 and inferior side 104. Gap 120 is shown as having a generally rectangular shaped in which its length (e.g., space between legs 116, 118) is greater than its width (e.g., length of legs 116, 118), but it should be understood that gap 120 may have a square shape in which the length and width dimensions are equal. Further, one of ordinary skill in the art will understand that gap 120 may have other shapes (e.g., arced, triangular, etc.) to facilitate visualization of the underlying bone. In some embodiments, a crossbar (not shown) may extend across gap 120, i.e., from leg 116 to leg 118. The crossbar may have a surface (e.g., a lower or inferior surface) that corresponds to a location of a potential resection line (e.g., the location at which a planar surface of a talus is formed) as will be described in greater detail below.

In some embodiments, each leg 116, 118 may include one or more holes and/or slots. For example, and as shown in FIGS. 2 and 3, leg 116 may define a first hole 122 and a second hole 124 located above (e.g., superior to) first hole 122, and leg 118 may define a first hole 126 and a second hole 128 located above (e.g., superior to) first hole 126. Holes 122, 124, 126, 128 are sized and configured to receive a pin or other engagement feature for coupling another surgical guide to guide 100. For example, holes 122, 124, 126, 128 may be sized and configured to receive an engagement feature for coupling an alignment guide, such as an angel wing alignment guide 200 described below and illustrated in FIGS. 8-14, to the guide 100, although one of ordinary skill in the art will understand that other guides or surgical device may be coupled to guide 100 via one or more holes 122, 124, 126, 128. One of ordinary skill in the art will understand that the features could be reversed, where the angel wing alignment guide 200 possess holes 122, 126 and guide 100 defines projections 210-1, 210-2.

In some embodiments, one of more of holes 122, 124, 126, 128 may be oblong or take the form of slots to facilitate proper alignment and coupling of other tools and guides. For example, in the example illustrated in FIGS. 1-7, holes 126, 128 are shown having an oblong shape, and it should be appreciated that one or more of the other holes 122, 124, 126, 128 or combinations of holes may have other forms and shapes.

Body 102 also defines a central opening 130 located between inferior side 104 and superior side 106. In some embodiments, one or more projections 134-1, 134-2 extend inwardly into opening 130. Projections 134-1, 134-2 collectively may be referred to as a "joint-line indicator 134," as they are located to provide a surgeon or other medical professional an indication as to the location of the joint line of a prosthesis that is to be implanted. While projections 134-1, 134-2 are shown as being pointed or arrow shaped, one of ordinary skill in the art will understand that the projections 134-1, 134-2 may take other shapes and forms to provide a joint line indicator 134.

In some embodiments, a number of holes are provided adjacent to superior side 106 of body 102 above opening 130. For example, body 102 may define holes 136, 138; holes 140, 142; and hole 144. Holes 136, 138 may be referred to as corner drill holes 136, 138 and be sized and configured to identify the location of the superior tibial resection intersections. Put another way, the corner drill holes 136, 138 are located at the superior medial and lateral corners of the tibial resection. In some embodiments, the corner drill holes 136, 138 may be used to guide a surgical tool, such as a drill, to perform work on bone (e.g., drill into bone).

Figure 16:
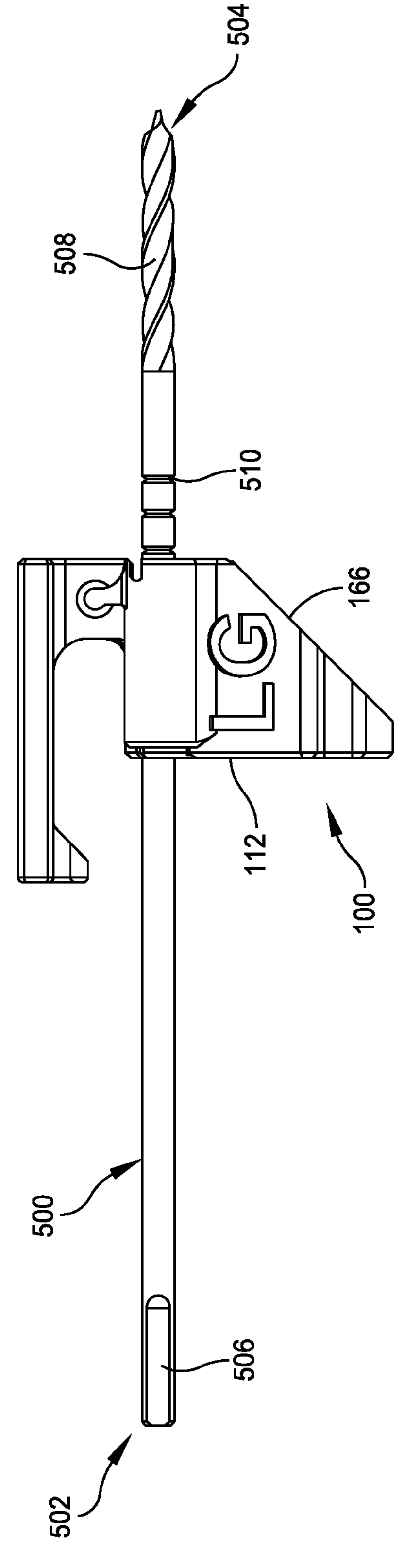
FIG. 16 is a side view of one example of the drill bit illustrated in FIG. 15 disposed within a hole defined by the guide illustrated in FIGS. 1-7, in accordance with some embodiments.
Figure 17:
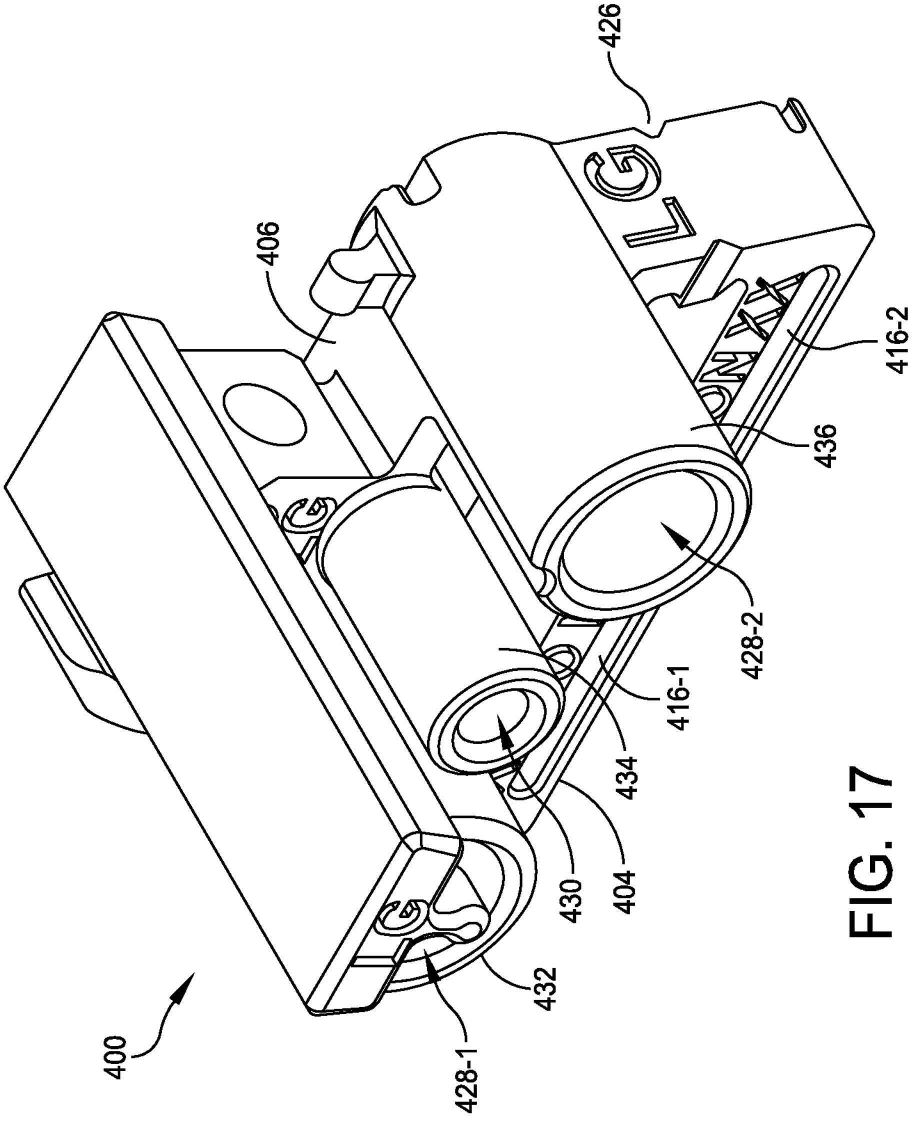
FIG. 17 is an isometric perspective view of another example of a guide in accordance with some embodiments.

Holes 140, 142 are shown as being positioned adjacent to holes 136, 138 such that hole 140 is located between hole 136 and hole 144 and hole 142 is located between hole 138 and hole 144. As will be understood by one of ordinary skill in the art, the position of holes 140, 142 could be located in various arrangements to facilitate boney fixation. Holes 140, 142 are sized and configured to receive a pin, k-wire, or other fixation device therein. As will be understood by one of ordinary skill in the art, a fixation device may be received within one or both of holes 140, 142 to secure guide 100 to bone. Hole 144 is sized and configured to receive a surgical tool, such as a drill bit, pin, and/or depth gauge, therein. For example, a pin, drill, or other surgical tool may be inserted into hole 144 to determine an appropriate length for an implant, as best seen in FIG. 16.

In some embodiments, guide 100 may include one or more alignment features, including one or more alignment features that extend superiorly from superior side 106. For example, a first alignment feature, which may be a sagittal alignment feature, may extend from superior side 106 and include at least a first component 150-1 and a second component 150-2. In some embodiments, the first component 150-1 takes the form of a block having a circular opening 152 (FIG. 5), and second component 150-2 takes the form of a projection that terminates in a circular shape 154 (FIG. 4). As best seen in FIGS. 4 and 5, when viewed from the side and the fluoroscope is properly aligned with the guide 100, the circular shape 154 will appear within an approximate center of the circular opening 152 defined by the first component 150-1 (e.g., a bullseye). If the fluoroscope is not properly aligned, then the circular shape 154 will not appear centered within circular opening 152. Although the first and second components 150-1, 150-2 are described as including circular shapes and openings, one of ordinary skill in the art will understand that other shapes, which may be complementary to one another, may be used to provide a fluoroscopic alignment check.

In some embodiments, guide 100 may include a second alignment feature, which may be a coronal alignment feature and may also extend from superior side 106. Second alignment feature includes a base 156 and a flange 158 that extends in an anterior direction from base 156. Base 156 defines a hole 160 that extends entirely through base 156, as best seen in FIG. 3. Flange 158 extends from base 156 in an anterior direction and includes a projection 162 along its length. In some embodiments, flange 158 has a trapezoidal cross-sectional geometry that is sized and configured to form a dovetail connection with another surgical tool, such as the adjustment block 300 with a tool holder 330 disclosed in U.S. Pat. No. 10,136,904, which was incorporated by reference in its entirety above. However, it should be understood that flange 158 may have other cross-sectional geometries to facilitate coupling to other surgical tools.

As best seen in FIG. 2, projection 162 extends from flange 158 in an inferior direction and terminates with a circular shape. When a fluoroscope is properly aligned with guide 100 in the coronal or frontal plane, projection 162 will appear to be disposed within the center of hole 160 (e.g., a bullseye) to provide a fluoroscopic alignment check. Although hole 160 and projection 162 are described and shown as having circular shapes, one of ordinary skill in the art will understand that hole 160 and projection 162 may have other shapes.

The location of base 156 along superior side 106 may be varied. For example, while base 156 is shown as being positioned along the posterior side 114, it should be understood that base 156 may be located closer to or at the anterior side 112 along superior side 106. In some embodiments, base 156 may define a second hole 164 that is aligned with circular opening 152 defined by first component 150-1 of the first alignment feature such that second component 150-2 may be visible through both circular opening 152 and hole 164, as best seen in FIG. 4. However, it should be understood that hole 164 may be omitted depending on the relative positioning of the first alignment feature and base 156.

Although the first and second alignment features are described as extending from superior side 106 of guide 100, it should be understood that the first and/or second alignment features may be otherwise located on guide 100. For example, one or both of the first and second alignment features may extend from other sides or surfaces of the guide, such as the anterior side 112, the inferior side 104 or may be otherwise incorporated into the body 102 of guide 100. Additionally or alternatively, the first and/or second alignment features may be positioned on another guide that may be coupled to guide 100. For example, the first, second, and/or additional alignment features could be disposed on or otherwise provided by the angel wing alignment guide 200, which is described in greater detail below.

Referring to FIGS. 4 and 5, it can be seen that the posterior side 114 may be angled or include a beveled surface 166. Beveled surface 166 may extend away from posterior side 114 in an anterior direction to provide clearance for the talus when guide 100 is positioned against a tibia. In some embodiments, posterior side 114 may include a notch or slot 168 that extends inwardly (e.g., in an anterior direction). Notch 168 is aligned with the surface of superior side 106 and provides a visual indicator as to the upper surface of a prosthesis (not shown) that corresponds to guide 100. For example, guide 100 may be provided in one or more sizes, which corresponding to one or more sizes of available implants, such as a tibial implant of a total ankle prosthesis. When guide 100 is viewed under fluoroscopy in the sagittal plane, notch 168 provides the surgeon with an indication as to where the tibia will be resected and where the upper (e.g., superior) surface of the tibial component of the ankle prosthesis will be located. One or more additional notches may be provided along the posterior side 114 to identify the location of the lower (e.g., inferior) surface of the tibial component or talar component or upper (e.g., superior) surface of the talar component, as will be understood by one of ordinary skill in the art. Further, it should be understood that while notch 168 is shown being located along the posterior side 114 so that the notch is positioned adjacent to bone, other types of visual indicators may be used and placed at other locations on body 102 of guide 100.

Guide 100 may include other visualization indicators. For example and referring again to FIGS. 2 and 3, legs 116, 118 may include one or more steps, such as steps 170-1, 170-2, 172-1, 172-2, for providing a surgeon with a visual indication as to the location of a lower or upper surface of a prosthesis (e.g., a talar prosthesis). As noted above, in some embodiments, multiple implant sizes may be provided, including sizes having multiple heights, e.g., short and tall heights. Steps 170-1, 170-2 (collectively, "steps 170") may correspond to a short or chamfer sized implant, and steps 172-1, 172-2 (collectively, "steps 172") may correspond to a tall or flat-top implant. Further, in some embodiments, a respective surface of steps 170 may be coplanar with the inferior surface 104, and steps 172 may be coplanar with a crossbar (not shown) that extends between legs 116, 116, if provided.

In some embodiments, the guide 100 may include one or more indicia, such as indicia 174-1, 174-2 (collectively, "indicia 174") located on the anterior side 112 (FIG. 2), indicia 176 located on side 108 (FIG. 5), and indicia 178 located on side 110 (FIG. 4). One or more of indicia 174, 176, 178 may be visible both with or without fluoroscopy. Providing indicia that is visible under fluoroscopy advantageously enables the indicia to be visible on x-rays or other fluoroscopically obtained images so that a surgeon and/or other healthcare professional may be able to compare the relative sizes of the guides and thus assess what size implant should be used with the patient.

Figure 9:
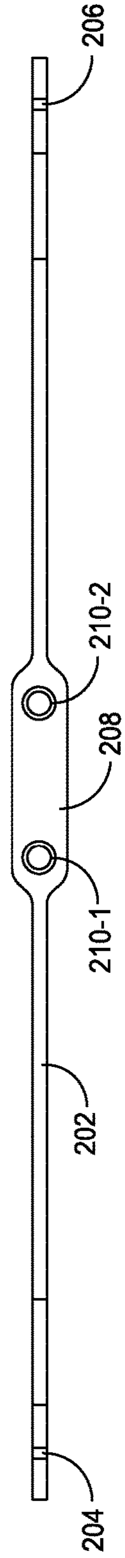
FIG. 9 is a rear end view of the alignment guide illustrated in FIG. 8 in accordance with some embodiments.
Figure 8:
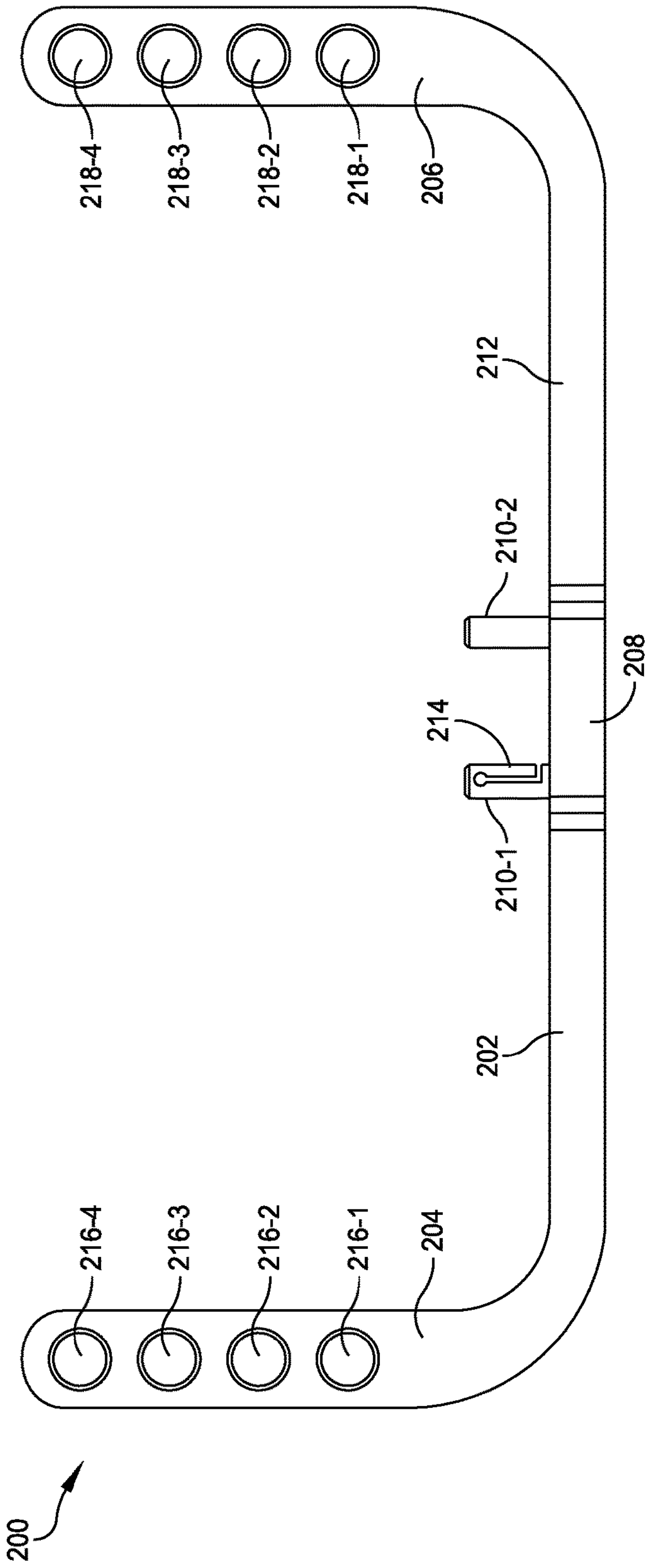
FIG. 8 is a top side view of one example of an alignment guide in accordance with some embodiments.
Figure 10:
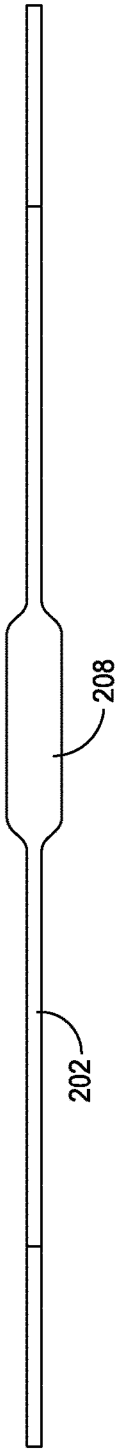
FIG. 10 is a front end view of the alignment guide illustrated in FIG. 8 in accordance with some embodiments.

Turning now to FIGS. 8-10, one example of an angel wing alignment guide 200 is illustrated. As noted above and described in greater detail below, the angel wing alignment guide 200 may be used in combination with guide 100. Alignment guide 200 may have a generally arcuate or "u-shaped" body with a transverse beam 202 extending between a first arm 204 and a second arm 206. As best seen in FIGS. 9 and 10, the transverse beam 202 may include an enlarged area 208, which may have a width that is greater than a width of a remainder of the transverse beam 202 and/or a width of arms 204, 206. In some embodiments, one or more dowels or protrusions 210-1, 210-2 (collectively, "dowels 210" or "protrusions 210") extend from a posterior surface 212 of alignment guide 200. Protrusions 210 are sized and configured to be received within holes 122, 124, 126, 128 defined by the legs 116, 118 of guide 100 for coupling the alignment guide 200 to guide 100. As best seen in FIG. 8, one or both of the protrusions 210 may include a spring arm, detent, or other coupling mechanism 214 for increasing the frictional coupling between the protrusion(s) 210 and holes 122, 124, 126, 128 and thus between alignment guide 200 and guide 100. One of ordinary skill in the art will understand that while the protrusions 210 are shown as having a generally circular cross-sectional shape, which a cross section is taken along an axis perpendicular to a longitudinal axis of the protrusions, the protrusions 210 may have other cross-sectional shapes, e.g., triangular, rectangular, etc.

In some embodiments, arm 204 includes one or more holes 216-1, 216-2, 216-3, 216-4 (collectively, "holes 216"), and arm 206 includes one or more holes 218-1, 218-2, 218-3, 218-4 (collectively, "holes 218"). Holes 216, 218 are sized and configured to receive a dowel, pin, rod, or other elongate radiopaque device. The elongate radiopaque device may be coupled to the alignment guide 200 to provide a surgeon with an approximation of an axis of a tibial implant that is to be implant such that the surgeon can assess the proper location of a cutting and/or reaming guide with a mechanical and/or anatomic axis of the patient. Although plural holes are shown in FIG. 8 to provide the surgeon with multiple locations at which the alignment rod may be positioned, it should be understood that a single hole may be provided, or one or more slots may be provided along the longitudinal axes of the arms 204, 206 to provide the surgeon with the ability to provide near continuous adjustment of the location of such an alignment rod.

As noted above, the alignment guide 200 may include one or more alignment features, such as the sagittal and/or coronal alignment features discussed above. For example, the first and second components 150-1, 150-2 of the first alignment feature may be provided along the arms 204, 206 and/or transverse beam 202. Additionally or alternatively, the base 156 and/or flange 158 of the second alignment feature may be provided along arms 204, 206 and/or transverse beam 202, as will be understood by one of ordinary skill in the art.

Figure 11:
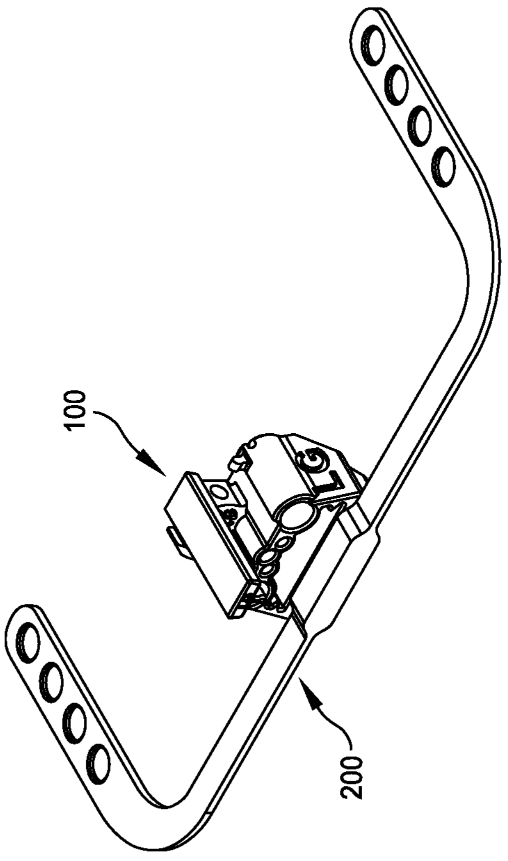
FIG. 11 is an isometric view of one example of the alignment guide illustrated in FIG. 8 coupled to the guide illustrated in FIG. 1 in a first position, in accordance with some embodiments.
Figure 12:
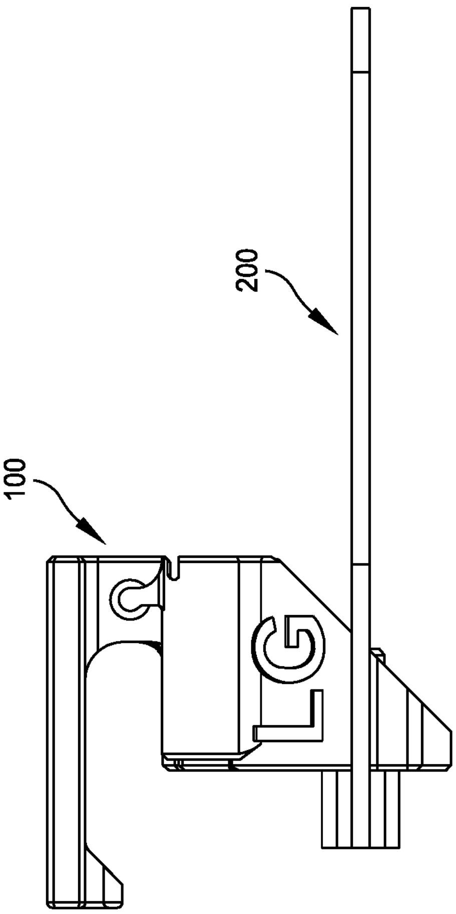
FIG. 12 is a side view of the alignment guide illustrated in FIG. 8 coupled to the guide illustrated in FIG. 1 in a first position, in accordance with some embodiments.

FIGS. 11 and 12 illustrate one example of alignment guide 200 coupled to guide 100. More particularly, in FIGS. 11 and 12, the protrusions 210 of alignment guide 200 are disposed within holes 124, 128 of guide 100. In some embodiments, a surface (e.g., a bottom or top surface) of one or more of arms 204, 206 may be aligned with steps 170 when protrusions 210 of alignment guide 200 are disposed within holes 124, 128 of guide 100. As such, the surface(s) of arms 204, 206 may provide a visual indication of a location of an inferior surface of an implant (e.g., a talar implant) and/or a location at which a talus will be resected.

Figure 14:
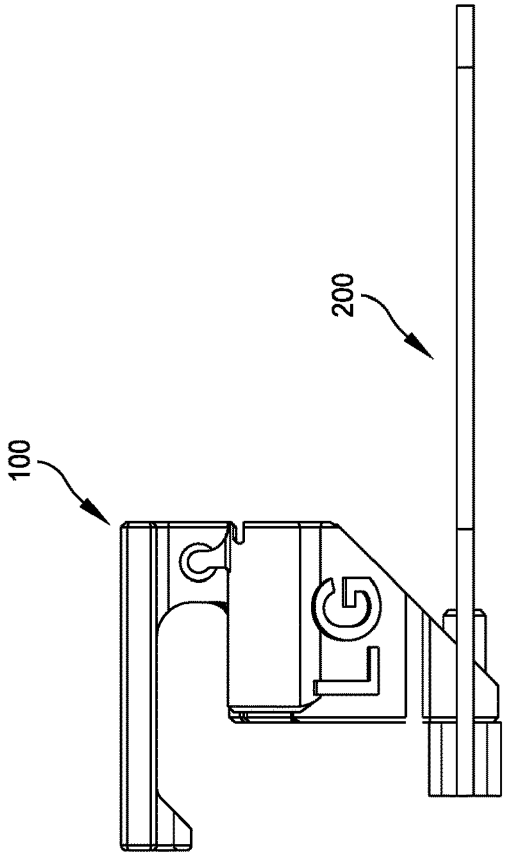
FIG. 14 is a side view of the alignment guide illustrated in FIG. 8 coupled to the guide illustrated in FIG. 1 in the second position, in accordance with some embodiments.
Figure 13:
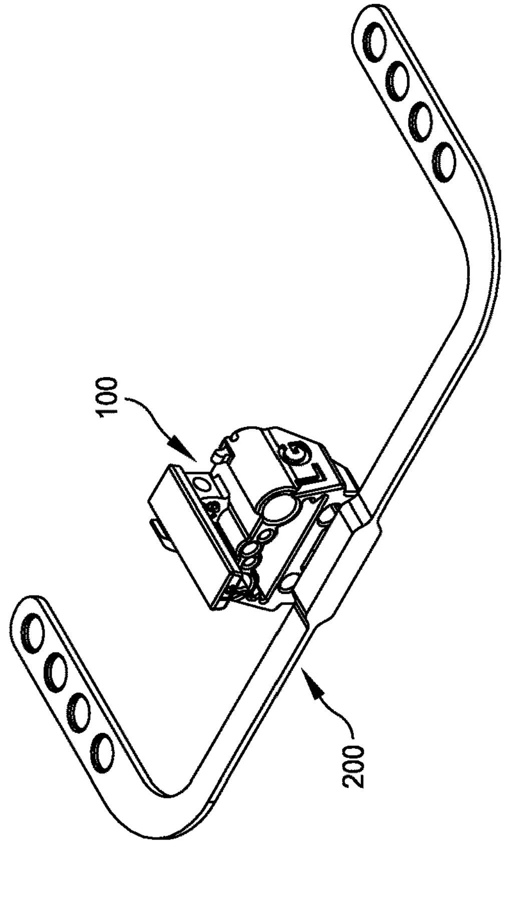
FIG. 13 is an isometric view of one example of the alignment guide illustrated in FIG. 8 coupled to the guide illustrated in FIG. 1 in a second position, in accordance with some embodiments.

FIGS. 13 and 14 illustrate another example of alignment guide 200 coupled to guide 100. More particularly, in FIGS. 13 and 14, the protrusions 210 of alignment guide 200 are disposed within holes 122, 126 of guide 100. In some embodiments, a surface (e.g., a bottom or top surface) of one or more of arms 204, 206 may be aligned with steps 172 when protrusions 210 of alignment guide 200 are disposed within holes 122, 126 of guide 100. As such, the surface(s) of arms 204, 206 may provide a visual indication of a location of an inferior surface of an implant (e.g., a talar implant) and/or a location at which a talus will be resected.

Figure 15:
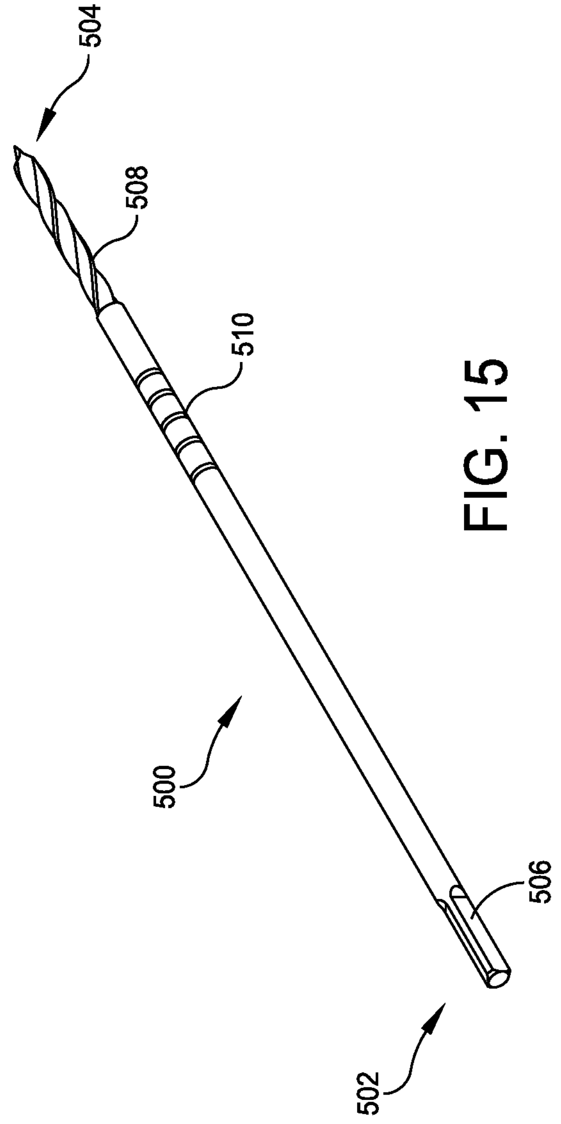
FIG. 15 is an isometric perspective view of one example of a drill bit that may be used with a guide in accordance with some embodiments.

Turning now to FIG. 15, one example of a drill bit 500 that may be used with guide 100 is illustrated. Drill bit 500 extends from a first end 502, which may also be referred to as a "coupling end" or a "trailing end," to a second end 504, which may also be referred to as a "drilling end" or a "leading end." Coupling end 502 may include one or more flats 506 or other surfaces that facilitate engagement with a power system or hand tool as will be understood by one of ordinary skill in the art. Leading end 504 may include one or more threads or cutting elements 508 to facilitate a drilling operation. Drill bit 500 may further include one or more grooves or other indicia 510 disposed along a length of the drill bit 500. For example, indicia 510 may include numerals and/or letters in addition to grooves, as will be understood by one of ordinary skill in the art. In some embodiments, the one or more indicia 510 is located between an approximate middle of drill bit 500 and a proximal end of cutting element(s) 508.

FIG. 16 illustrates one example of the drill bit 500 disposed within hole 144 defined by guide 100. In use, one or more of the indicia 510 are visible when the assemblage of the guide 100 and drill bit 500 are viewed in the sagittal plane under fluoroscopy. The indicia 510 identify a depth of the tip of the drill bit 500, which may correspond to a length of a prosthesis component. For example, in some embodiments, the indicia correspond to a length of a tibial tray of a total ankle prosthesis, such as the tibial tray of the INBONE™ total ankle prosthesis.

Figure 20:
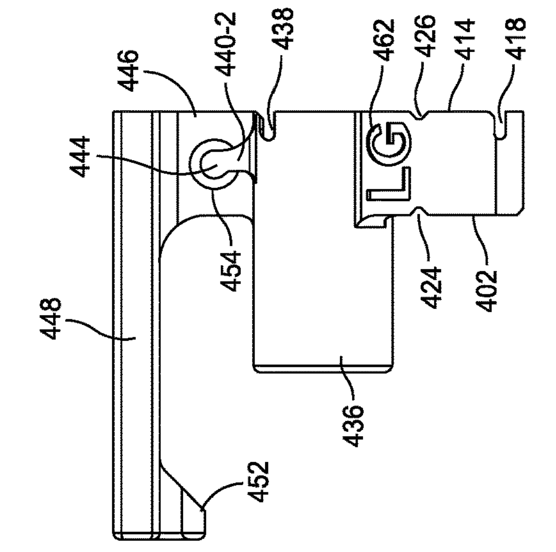
FIG. 20 is a side view that is opposite the side view illustrated in FIG. 19 of the guide illustrated in FIG. 17 in accordance with some embodiments.
Figure 18:
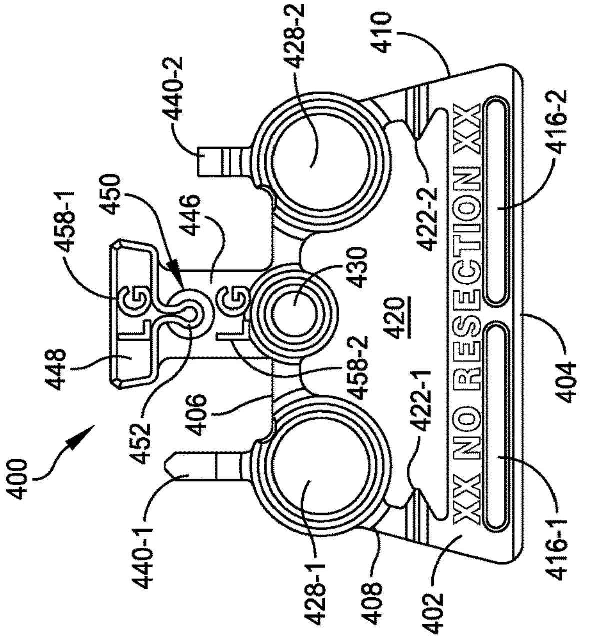
FIG. 18 is a front side view of the guide illustrated in FIG. 17 in accordance with some embodiments.
Figure 19:
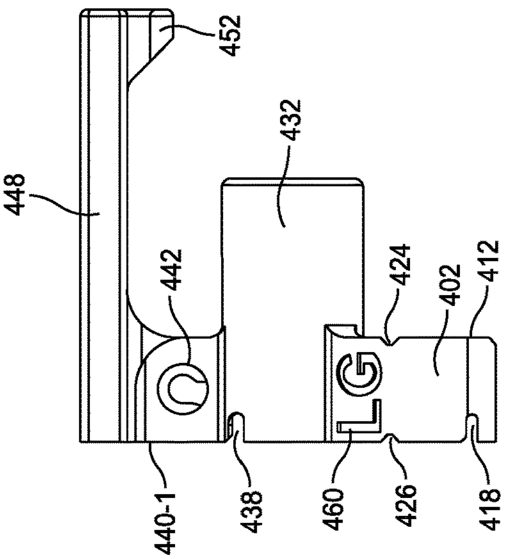
FIG. 19 is a side view of the guide illustrated in FIG. 17 in accordance with some embodiments.
Figure 22:
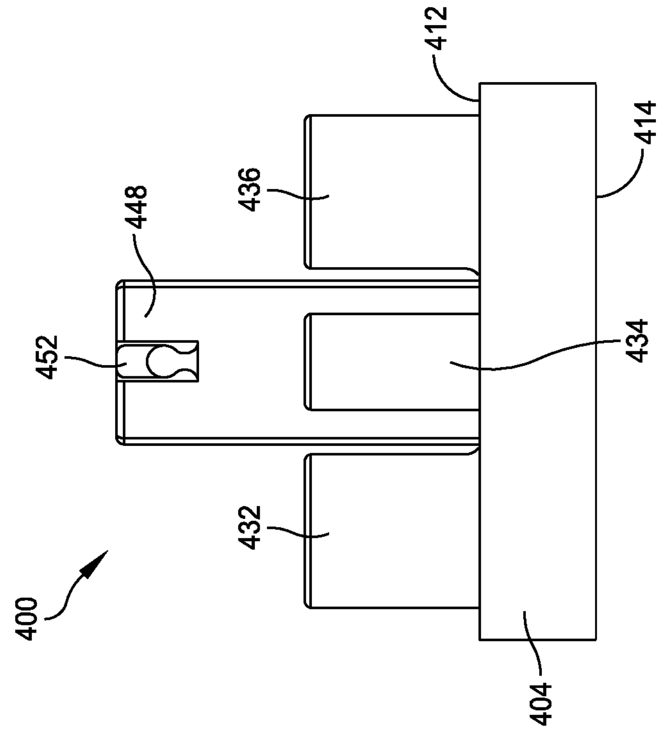
FIG. 22 is a bottom side view of the guide illustrated in FIG. 17 in accordance with some embodiments.
Figure 21:
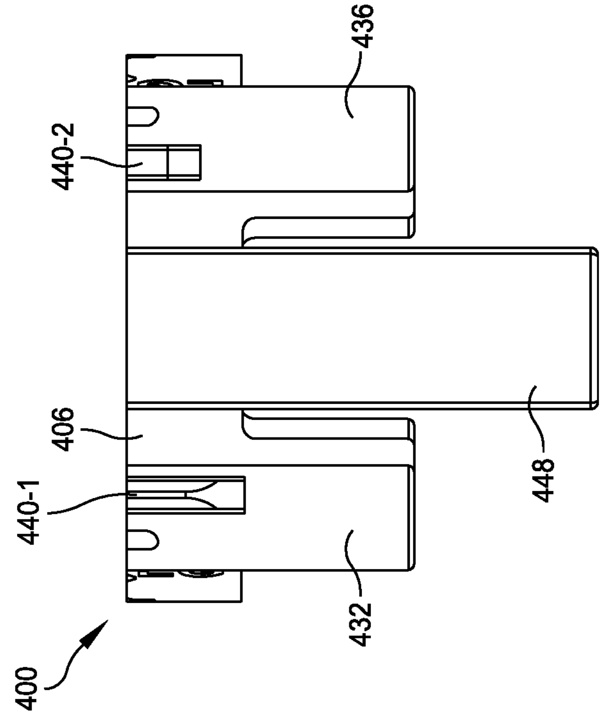
FIG. 21 is a top side view of the guide illustrated in FIG. 17 in accordance with some embodiments.

FIGS. 17-22 illustrate another example of a sizing and drill guide 400 in accordance with some embodiments. Guide 400 includes a body 402 extending from an inferior side 404 to a superior side 406, as best seen in FIG. 18. Body 402 further includes opposed sides 408, 410 (FIG. 18), an anterior side 412, and a posterior side 414, as best seen in FIGS. 19 and 20. The profile of guide 400, such as defined by inferior side 404, superior side 406, and opposed sides 408, 410, which is shown as having a generally trapezoidal shape, may correspond to the profile of a prosthesis component. For example, the profile of guide 400 defined by inferior side 404, superior side 406, and opposed sides 408, 410 may correspond to the tibial and/or talar prosthesis components of a total ankle replacement system, although one of ordinary skill in the art will understand that body 402 of guide 400 may have a shape that corresponds to other types of implants.

In some embodiments, body 402 may be formed from a rigid radiopaque material, such as a surgical grade metal. One of ordinary skill in the art will understand that guide 400 may be formed from other materials, such as a combination of radiolucent (e.g., Radel® polyphenylsulfone (PPSU), available from Solvay) and radiopaque (e.g., stainless steel, aluminum, titanium, cobalt, chromium) materials. Guide 400 may be machined from a single block of material, molded, or formed using an additive manufacturing process (e.g., DMLS, EBM).

One or more slots 416-1, 416-2 (collectively, "slots 416") may be defined by body 402 adjacent to the inferior side 404. Slots 416 extend from the anterior side 412 of body 402 to the posterior side 414 of body 402 and are sized and configured to receive a resection level indicator and/or blade of a cutting instrument, such as a saw. In some embodiments, slots 416 are aligned with one another such that a longitudinal axis defined by slot 416-1 is collinear with a longitudinal axis defined by slot 416-2, although it should be understood that slots 416 may be otherwise arranged with respect to one another. As best seen in FIGS. 19 and 20, the posterior side 414 may include one or more notches 418, which are aligned with slots 416, and one or more notches 438, which are aligned with the superior surface 406 of body 402. The one or more notches 418 provide a surgeon or other medical professional with a visual indication as to the location of the slots 416, which may correspond to the location of a bone resection and/or an inferior surface of an implant based on the positioning of the guide 400 when guide 400 is viewed under fluoroscopy in the sagittal plane. Similarly, the one or more notches 438 may provide a surgeon or other medical professional with a visual indication as to the location of the superior surface of the body 402, which may correspond to a superior surface of an implant, such as the tibial implant of a total ankle prosthesis.

Body 402 may also define a central opening 420 located between inferior side 404 and superior side 406 and between opposed sides 408, 410. In some embodiments, one or more projections 422-1, 422-2, which collectively may be referred to as "projections 422" or "joint-line indicator 422," extend inwardly into opening 420. Projections 422 are located along body 402 to provide a surgeon or other medical professional a visual indication as to the location of the joint line of a prosthesis, such as a total ankle prosthesis, that is to be implanted when viewed in the frontal plane. While projections 422 are shown as being pointed or arrow shaped, one of ordinary skill in the art will understand that the projections 422 may take other shapes and forms to provide a joint line indicator 422. As best seen in FIGS. 19 and 20, the anterior side 412 and posterior side 414 may respectively include notches 424, 426, which are aligned with joint-line indicator 422. Notches 424, 426 provide a surgeon or other medical professional with a visual indication as to the location of the joint line when guide 400 is viewed under fluoroscopy in the sagittal plane.

Figure 23:
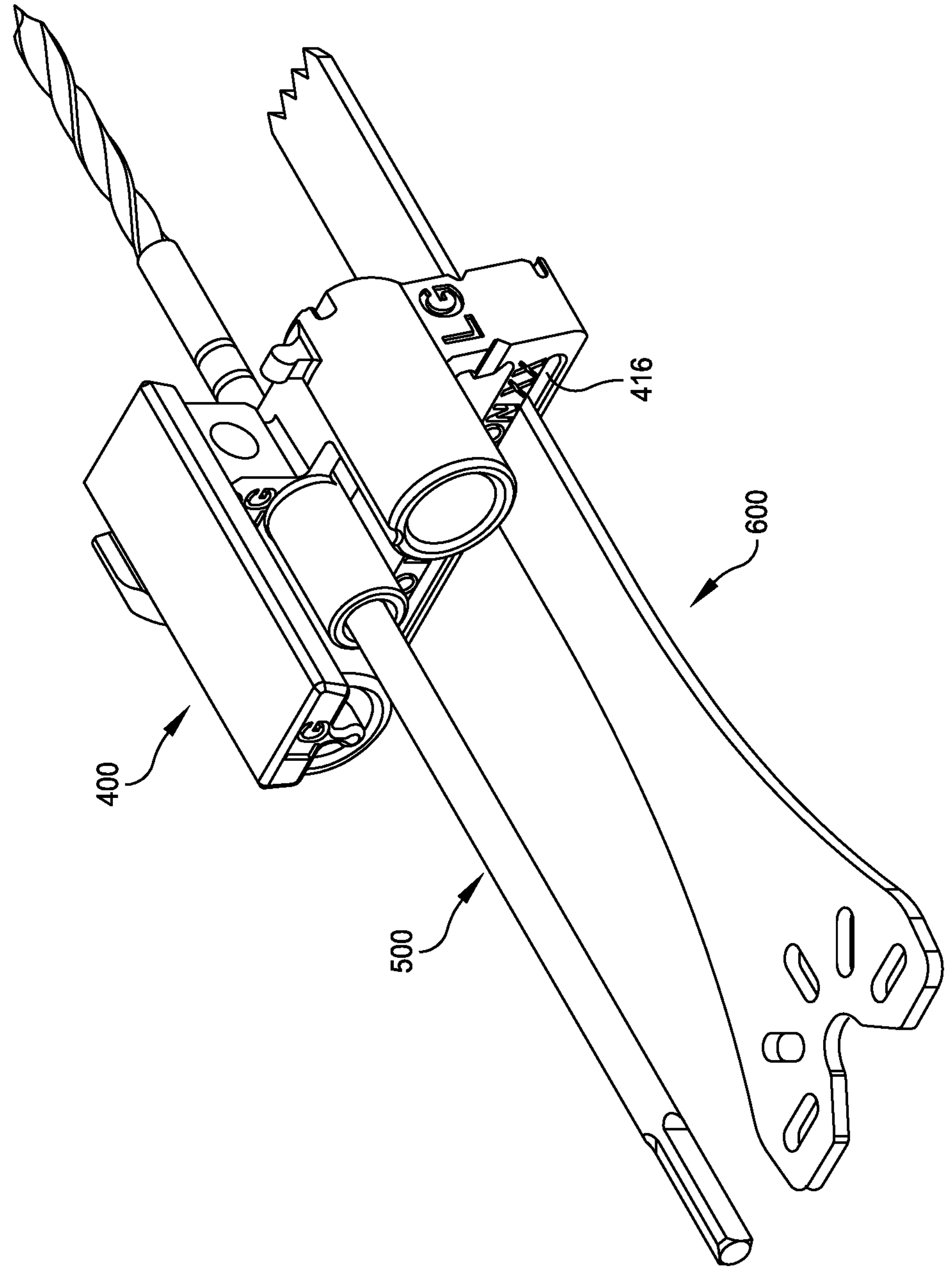
FIG. 23 is an isometric perspective view of the drill bit illustrated in FIG. 15 and a saw blade respectively disposed within a hole and a slot defined by the guide illustrated in FIG. 17 in accordance with some embodiments.
Figure 24:
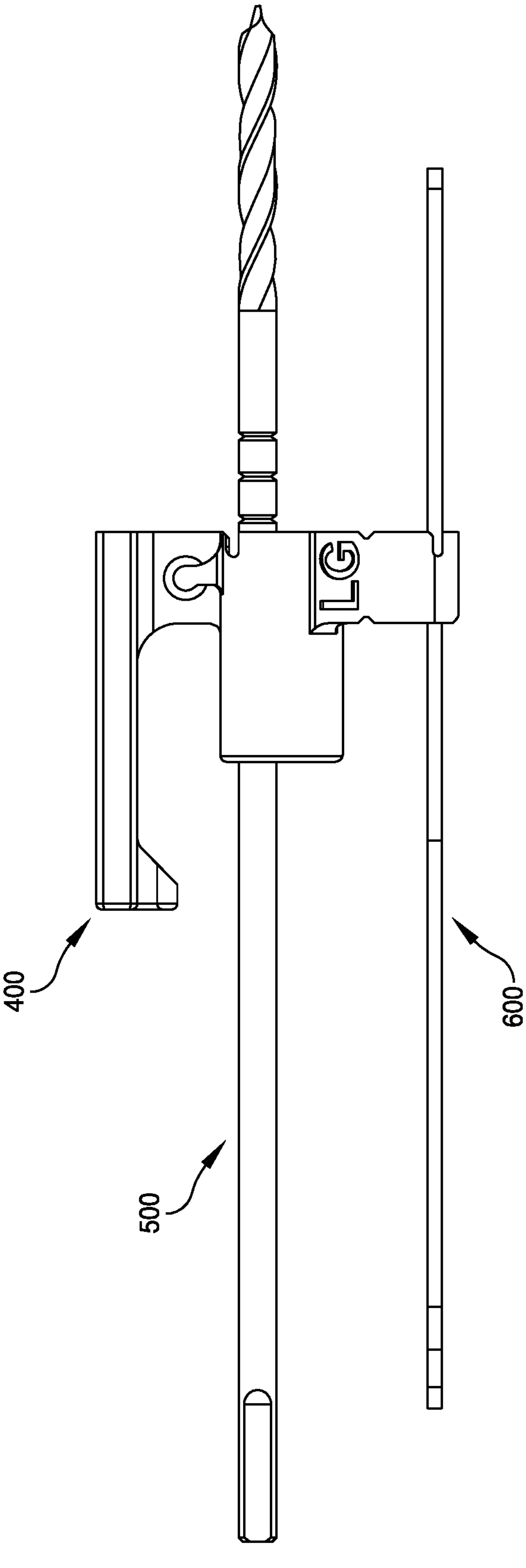
FIG. 24 is a side view of the drill bit illustrated in FIG. 15 and a saw blade respectively disposed within a hole and a slot defined by the guide illustrated in FIG. 17 in accordance with some embodiments.

Referring again to FIGS. 17 and 18, a number of holes may be provided adjacent to the superior side 406 of body 402 above opening 420. For example, body 402 may define corner drill holes 428-1, 428-2 (collectively, "holes 428" or "corner drill holes 428") and a central hole 430. Corner drill holes 428 may be sized and configured to receive a drill bit and/or to identify a location of where a drill is used to prepare the corners of a tibial resection. Put another way, the corner drill holes 428 are located at the superior medial and lateral corners of the tibial resection. Hole 430 may be sized and configured to receive a surgical tool, such as a drill bit, pin, and/or depth gauge, therein. For example, a pin, drill, or other surgical tool may be inserted into hole 430 to determine an appropriate length for an implant, as best seen in FIGS. 23 and 24. In some embodiments, holes 428, 430 may be formed in portions of body 402 that extend from anterior side 412 to form bushings 432, 434, 436. It should be understood that body 402 may define additional holes, such as holes to receive fixation elements (e.g., pins, k-wires, or any other suitable device) therein for securing the guide 400 to bone or other tissue.

Guide 400 may also include one or more alignment features. For example, guide 400 may include a first alignment feature, which may be a sagittal alignment feature, and a second alignment feature, which may be a coronal alignment feature. First alignment feature may extend superiorly from superior side 406 and include a first component 440-1 and a second component 440-2. In some embodiments, the first component 440-1 takes the form of a block having a circular opening 442 (FIG. 19), and component 440-2 takes the form of a projection that terminates in a circular shape 444 (FIG. 20). As best seen in FIGS. 19 and 20, when viewed from the side and the fluoroscope is properly aligned with the guide 400, the circular shape 444 will appear within an approximate center of the circular opening 442 defined by the first component 440-1 to form a fluoroscopic check (e.g., a bullseye). If the fluoroscope is not properly aligned, then the circular shape 444 will not appear centered within circular opening 442. Although the first and second components 440-1, 440-2 are described as including circular shapes and openings, one of ordinary skill in the art will understand that other shapes may be used to provide a fluoroscopic alignment check.

Second alignment feature may include a base 446 and a flange 448 that extends in an anterior direction from base 446. Base 446 defines a hole 450 that extends entirely through base 446, as best seen in FIG. 18. Flange 448 extends from base 446 in an anterior direction and includes a projection 452 along its length. In some embodiments, flange 448 has a trapezoidal cross-sectional geometry that is sized and configured to form a dovetail connection with another surgical tool, such as the adjustment block 300 with a tool holder 330 disclosed in U.S. Pat. No. 10,136,904, which was incorporated by reference in its entirety above. However, it should be understood that flange 448 may have other cross-sectional geometries to facilitate coupling to other surgical tools. As best seen in FIG. 18, projection 452 extends from flange 448 in an inferior direction and terminates with a circular shape. When a fluoroscope is properly aligned with guide 400 in the coronal or frontal plane, projection 452 will appear to be disposed within the center of hole 450 (e.g., a bullseye) to provide a fluoroscopic alignment check. Although hole 450 and projection 452 are described and shown as having circular shapes, one of ordinary skill in the art will understand that hole 450 and projection 452 may have other shapes.

The location of base 446 along superior side 406 may be varied. For example, while base 446 is shown as being positioned along the posterior side 414, it should be understood that base 446 may be located closer to or at the anterior side 412 of body 402. In some embodiments, base 446 may define a second hole 454 that is aligned with circular opening 442 defined by first component 440-1 of the first alignment feature such that second component 440-2 may be visible through both circular opening 442 and hole 454, as best seen in FIG. 20. However, it should be understood that hole 454 may be omitted depending on the relative positioning of the first alignment feature and base 446.

Although the first and second alignment features are described as extending from superior side 406 of guide 400, it should be understood that the first and/or second alignment features may be otherwise located on guide 400. For example, one or both of the first and second alignment features may extend from other sides or surfaces of guide 400, such as the anterior side 412, the inferior side 404 or may be otherwise incorporated into the body 402 of guide 400.

In some embodiments, the guide 400 may include one or more indicia, such as indicia 458-1, 458-2 (collectively, "indicia 458") located on anterior side 412, indicia 460 located on side 408 (FIG. 19), and indicia 462 located on side 410 (FIG. 20). One or more of indicia 458, 460, 462 may be visible both with or without fluoroscopy. Providing indicia that is visible under fluoroscopy advantageously enables the indicia to be visible on x-rays or other fluoroscopically obtained images so that a surgeon and/or other healthcare professional may be able to compare the relative sizes of the guides and thus assess what size implant should be used with the patient.

FIGS. 23 and 24 illustrate one example of the drill bit 500 disposed within hole 430 defined by guide 400 and a saw blade 600 disposed within one of the slots 416. As discussed above with respect to guide 100, the indicia 510 of drill bit 500 are visible when viewed in the sagittal plane under fluoroscopy. The indicia 510 identify a depth of the tip of the drill bit, which may correspond to a length of a prosthesis component.

Although guides 100, 400 are described separately and with some different features, it should be understood that guides 100, 400 may be modified to include additional features, including features from the other guide. For example, guide 400 may be modified to include legs 116, 118 and/or a posterior surface having a taper or bevel 166, as described above with respect to guide 100. Additionally or alternatively, guide 100 may be modified to include one or more of notches 418, 426 to provide visualization queues to a surgeon or other medical professional.

The guides described herein may be used by a surgeon or other medical professional to assess a size of a prosthesis to be implanted into a patient. In some embodiments, the guides may also be used to perform corner drilling in order to prepare a tibia for resection and receipt of a prosthesis. While the following description is provided with reference to the guide 100 illustrated in FIGS. 1-7, it should be understood that the following description of one example of a method of using guide 100 is applicable to guide 400, as well as other guides in accordance with the present disclosure.

Figure 25:
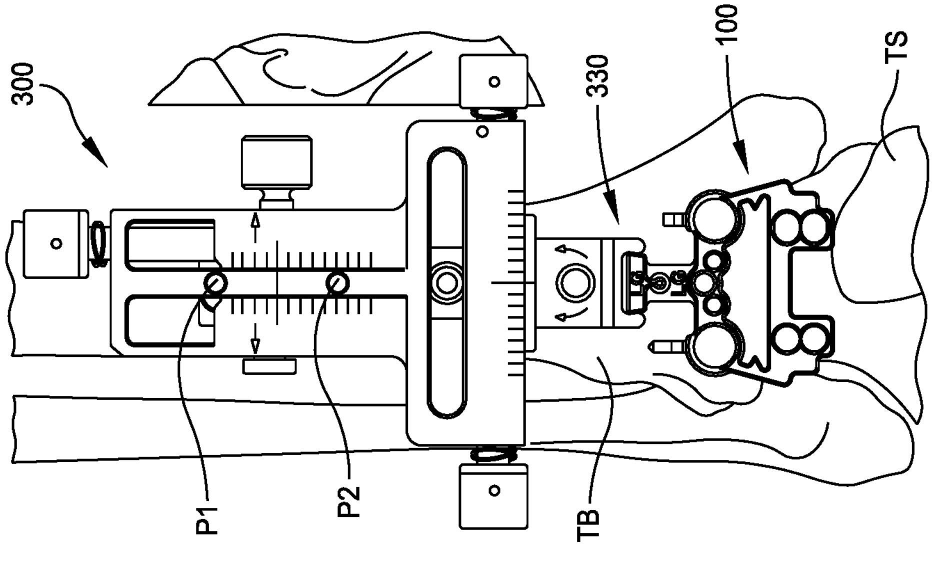
FIG. 25 illustrates one example of a guide being coupled to an adjustment block that is secured to a tibia, in accordance with some embodiments.

In some embodiments, guide 100 is coupled to another surgical tool previously placed on a tibia TB of a patient. For example and as illustrated in FIG. 25, guide 100 may be coupled to the tool holder 330 of adjustment block 300 disclosed in in U.S. Pat. No. 10,136,904, which is secured to the tibia TB by pins P1, P2. In some embodiments, flange 158, which may have a trapezoidal shape, is received between the rails of tool holder 330 to form a dovetail connection. The position of guide 100 may be adjusted using adjustment block 300, as described in U.S. Pat. No. 10,136,904.

The position of guide 100 may be adjusted in order to assess the sizing and/or alignment of guide 100 relative to the tibia TB and/or talus TS. For example, profile of the guide, such as provided by the inferior side 104, superior side 106, and opposed sides 108, 110, which may correspond to a profile of a tibial implant, may be used to assess whether the size of the corresponding implant is appropriate for the patient in the frontal plane and/or sagittal plane. Sizing of the implant in the sagittal plane may be performed by a surgeon or other medical professional with the assistance of one or more notches 168 and/or alignment guide 200, which may be located on guide 100 such that they correspond to the superior side 106 and/or inferior side 104. Such assessment may be performed using fluoroscopy. In order to ensure that the fluoroscope is properly aligned with guide 100, one or more of the first and second alignment features may be used to ensure proper alignment of the fluoroscope and guide 100.

For example, the first alignment feature, which may be a sagittal alignment feature, may be used by checking that shape 154 of the second component 150-2 appears within an approximate center of opening 152 defined by the first component 150-1. If the fluoroscope is not properly aligned, then shape 154 will not appear centered within opening 152. Additionally or alternatively, the second alignment feature, which may be a coronal alignment feature, may be used to check proper alignment between the fluoroscope and the coronal or frontal plane. For example, when a fluoroscope is properly aligned with guide 100 in the coronal or frontal plane, projection 162 will appear to be disposed within the center of the hole 160.

A guide 200 may be coupled to the guide 100 while determining the size and/or alignment of an implant. For example, one or more protrusions 210 may be inserted into holes 122, 126 or holes 124, 128 defined by legs 116, 118 to couple alignment guide 200 to guide 100, as shown in FIGS. 11-14. As noted above, in some embodiments, a surface (e.g., a bottom or top surface) of one or more of arms 204, 206 may be aligned with steps 170 when protrusions 210 of alignment guide 200 are disposed within holes 124, 128 of guide 100. As such, the surface(s) of arms 204, 206 may provide a visual indication of a location of an inferior surface of an implant (e.g., a talar implant) and/or a location at which a talus will be resected. In some embodiments, a surface (e.g., a bottom or top surface) of one or more of arms 204, 206 may be aligned with steps 172 when protrusions 210 of alignment guide 200 are disposed within holes 122, 126 of guide 100. As such, the surface(s) of arms 204, 206 may provide a visual indication of a location of an inferior surface of an implant (e.g., a talar implant) and/or a location at which a talus will be resected. Further, an elongate radiopaque device may be inserted into one or more of the holes or slots 216, 218 defined by the arms 204, 206 of guide 200 to assess the alignment of guide 100 with an axis of the tibia TB (e.g., a mechanical and/or anatomic axis).

Figure 26:
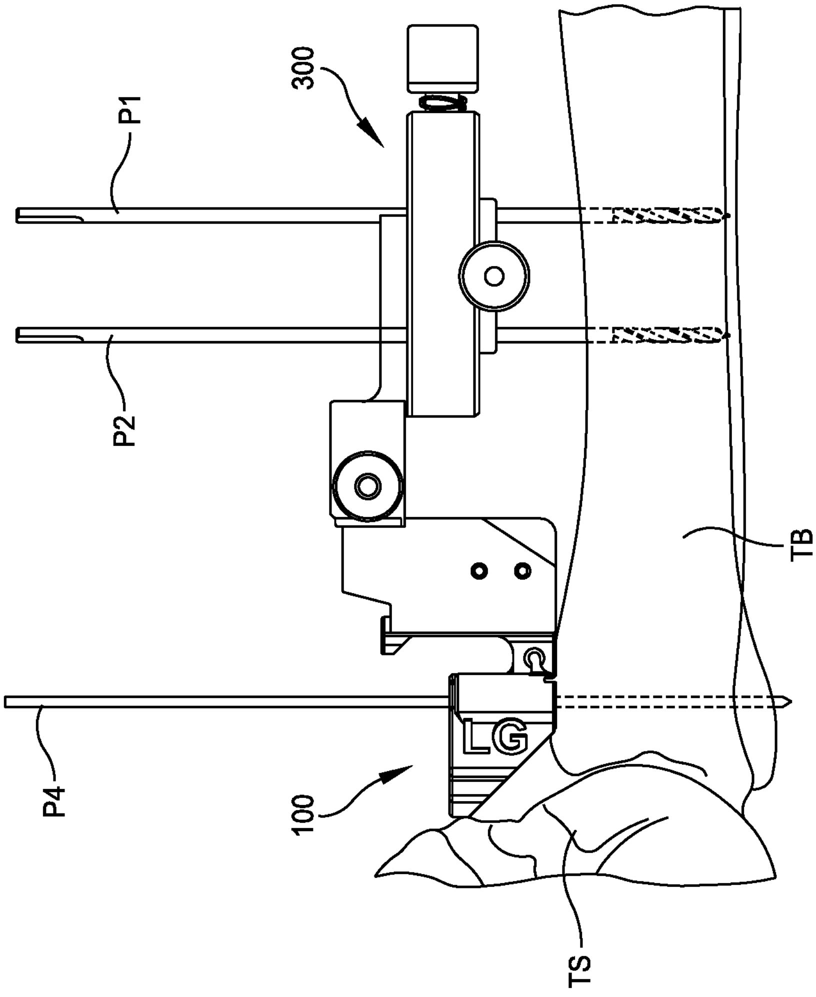
FIG. 26 illustrates one example of a pin inserted into a hole defined by a guide that is secured to a tibia, in accordance with some embodiments.
Figure 28:
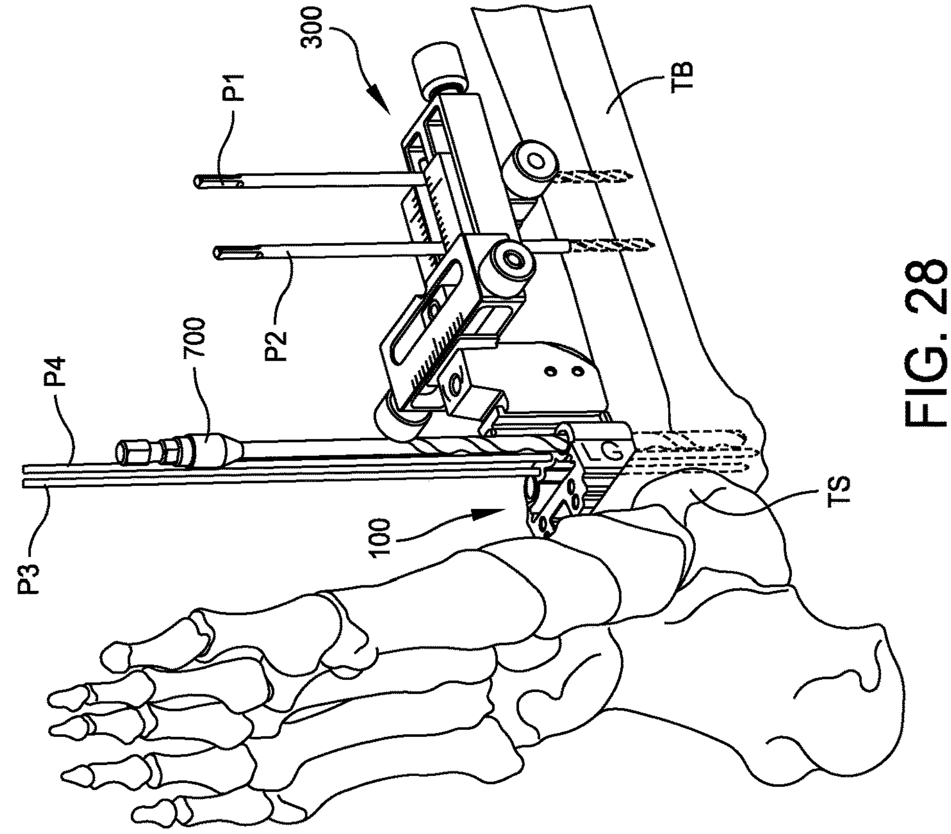
FIG. 28 illustrates one example of a guide being used to guide a drill for preparing a tibia for further resection, in accordance with some embodiments.
Figure 27:
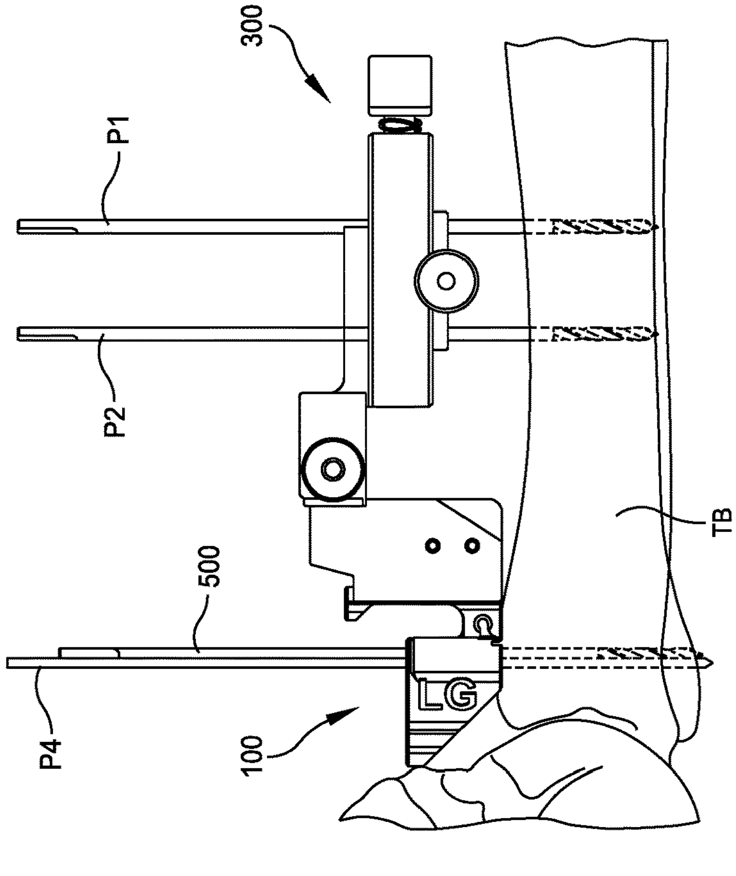
FIG. 27 illustrates one example of a drill bit being guided into a tibia by a first hole defined by a guide, in accordance with some embodiments.

When the size and desired location of the implant has been determined, guide 100 may be secured to the tibia TB by placing one or more pins P3, P4 in holes 140, 142, as shown in FIGS. 26-28. With guide 100 secured to tibia TB, drill bit 500 may be advanced into the tibia TB guided by hole 144, as illustrated in FIG. 27. Drill bit 500 may be advanced until it reaches the posterior surface of tibia TB. The location of the drill bit 500 may be determined using fluoroscopy as will be understood by one of ordinary skill in the art. Further, the length of the implant (e.g., anterior-to-posterior dimension) may be determined based on the visible indicia 510 located along the length of drill bit 500.

In some embodiments, once the size of the implant has been determined, guide 100 is used to drill the corners for the tibial resection. For example, a drill 700 may be inserted into corner drill holes 136, 138 and into the tibia TB, as shown in FIG. 28. Once the corner holes have been drilled, guide 100 may be removed from its engagement with the tibia TB and/or adjustment block 300. The tibia and talus may be further prepared using any suitable surgical technique, including the technique disclosed in U.S. Pat. No. 10,136,904, which was incorporated by reference above.

The disclosed guides, systems, and methods provide enhanced durability and have a reduced size, which improves the ability of the surgeon to manipulate the guide during surgery. Further, the disclosed guides, systems, and methods provide enhanced visibility of the surface(s) to be cut during the surgery while reducing the number of components used compared to conventional instrumentation, which yields a more streamlined and efficient method.

As described above, in some embodiments, a surgical guide includes a body having a shape that corresponds to a shape of an implant to be implanted. The body defines a first opening and at least one hole that is sized and configured to receive a tool therein. A first alignment feature is configured to facilitate alignment of the surgical guide with a first anatomic plane.

In some embodiments, an outer periphery of the body defines the shape that corresponds to the shape of the implant.

In some embodiments, the body includes a first side, a second side, a third side, and a fourth side, and the first opening is defined by the first side, the second side, the third side, and the fourth side.

In some embodiments, a second alignment feature is coupled to the body and is configured to facilitate alignment of the surgical guide with a second anatomic plane that is different from the first anatomic plane.

In some embodiments, first and second legs may extend from the first side of the body. Each of the first and second legs may define a respective hole that is sized and configured to receive a connection feature of another surgical guide.

In some embodiments, the connection feature includes a dowel.

In some embodiments, at least one of the first and second legs includes at least one step. The at least one step may provide a visual indication as to a location of a surface of a prosthesis to be implanted.

In some embodiments, the first and second legs include a plurality of steps.

In some embodiments, the first and second legs include a beveled surface.

In some embodiments, the first anatomic plane is a sagittal plane, and the second anatomic plane is a frontal plane.

In some embodiments, the first alignment feature includes a first component and a second component. The first component may include an opening, and the second component may include a projection that terminates in a shape that is complementary to a shape of the opening.

In some embodiments, the opening is defined by a block.

In some embodiments, the second alignment feature includes an opening and a projection that terminates in a shape that is complementary to a shape of the opening.

In some embodiments, the opening is defined by a block.

In some embodiments, the projection terminates from a flange that has a cross-sectional geometry to facilitate the coupling of the surgical guide to another surgical tool. In some embodiments, the cross-sectional geometry is trapezoidal.

In some embodiments, the at least one hole includes a first hole, a second hole, and a third hole disposed between the first hole and the second hole.

In some embodiments, the first hole is defined by a first bushing that extends from the body, the second hole is defined by a second bushing that extends from the body, and the third hole is defined by a third bushing that extends from the body.

In some embodiments, the body defines at least one slot that is disposed between the opening and the second side. The at least one slot may be sized and configured to receive a tool, including a depth indicating tool or a blade of a cutting tool.

In some embodiments, at least one of a posterior side or an anterior side of the body includes a notch configured to provide a visual indication of a location of at least one surface of a prosthesis to be implanted when the surgical guide is viewed in a sagittal plane.

In some embodiments, the body includes a joint line indicator.

In some embodiments, the joint line indicator includes at least one projection extending into the opening defined by the body.

In some embodiments, the joint line indicator includes a notch formed in at least one of a posterior side and/or an anterior side of the body.

In some embodiments, a first guide includes a first guide body having a first side, a second side, a third side, and a fourth side. The third and fourth sides extend between the first and second sides. The body defines a first opening between the first side, the second side, the third side, and the fourth side. The body may further define a first hole and a second hole each sized and configured to receive a fixation tool and/or and a cutting tool therein. A first alignment feature may extend from the second side of the body and be configured to facilitate alignment of the first guide with a first anatomic plane, and a second alignment feature may extend from the second side of the body and be configured to facilitate alignment of the first guide with a second anatomic plane. In some embodiments, the first anatomic plane and the second anatomic plane are the same. In some embodiments, the first anatomic plane and the second anatomic plane are different.

In some embodiments, the first guide includes first and second legs extending from the first side of the first guide body. A gap may be defined between the first leg, the second leg, and the first side of the first guide body.

In some embodiments, the system includes a second guide. The second guide may have a transverse beam that extends between a first arm and a second arm. The second guide may be configured to be coupled to the first guide.

In some embodiments, first and second protrusions extend from the transverse beam of the second guide. The first and second protrusions may be sized and configured to be received in respective connection features defined by the first and second legs of the first guide body for coupling the second guide to the first guide. In some embodiments, each connection feature includes a hole. In some embodiments, each connection feature includes a slot.

In some embodiments, each of the first and second arms of the second guide define at least one connection feature for receiving an elongate radiopaque device therein. In some embodiments, the at least one connection feature includes a hole. In some embodiments, the at least one connection feature includes a slot.

In some embodiments, the system includes a drill bit that extends from a first end to a second end. The first end may be configured to be coupled to a driving tool, and the second end may include at least one cutting surface. The drill bit may include at least one indicia located along its length at a distance from the second end. The distance of the at least one indicia from the second end may correspond to a length of an implant. The drill bit may be sized and configured to be received in a third hole defined by the first guide body.

In some embodiments, the third hole defined by the first guide body is located between the first hole and the second hole.

In some embodiments, the at least one indicia includes a plurality of indicia. Each indicia of the plurality of indicia may be disposed at a respective distance from the second end of the drill bit. The respective distance may correspond to a respective length of a different implant.

In some embodiments, a method includes coupling a first guide to an adjustment block, aligning a fluoroscope with the first guide in at least one anatomic plane using at least one of a first alignment feature and a second alignment feature of the first guide, coupling a second guide, and securing the first guide to a tibia once a desired alignment of the first guide has been achieved. In some embodiments, the second guide includes first and second arms that are coupled together by a transverse beam.

In some embodiments, coupling the second guide to the first guide includes inserting at least one protrusion extending from the transverse beam of the second guide into at least one connection feature of the first guide. In some embodiments, the at least one connection feature of the first guide includes at least one hole defined by the first guide. In some embodiments, the at least one connection feature of the first guide includes at least one slot defined by the first guide.

In some embodiments, a method includes determining a size of an implant to be implanted. The determining may be based at least in part on view of the first guide under fluoroscopy.

In some embodiments, determining the size of the implant includes inserting a drill bit into a hole defined by the first guide and into the tibia, and identifying an indicia disposed along a length of the drill bit.

In some embodiments, a method includes preparing a tibia for resection by inserting a drill into a first corner drill hole defined by the first guide.

In some embodiments, a method includes inserting the drill into a second corner drill hole defined by the first guide.

Although the guides, systems, and methods have been described in terms of exemplary embodiments, they are not limited thereto. Rather, the appended claims should be construed broadly, to include other variants and embodiments of the guides, systems, and methods, which may be made by those skilled in the art without departing from the scope and range of equivalents of the guides, systems, and methods.

What is claimed is:

1. A surgical guide, comprising:

a body having a shape that corresponds to a shape of an implant to be implanted, the body defining a first opening and at least one hole that is sized and configured to receive a tool therein; and a first alignment feature coupled to at least one side of the body and configured to facilitate alignment of the surgical guide with a first anatomic plane, wherein the first alignment feature includes a first component and a second component, the first component including a second opening, and the second component including a projection that terminates in a shape that is complementary to a shape of the second opening.

2. The surgical guide of claim 1, further comprising a second alignment feature coupled to the body and configured to facilitate alignment of the surgical guide with a second anatomic plane that is different from the first anatomic plane.

3. The surgical guide of claim 2, wherein the body includes a first side, a second side, a third side, and a fourth side, and wherein the first alignment feature extends from the second side of the body.

4. The surgical guide of claim 3, wherein the second alignment feature extends from the second side of the body.

5. The surgical guide of claim 3, wherein first and second legs extend from the first side of the body, each of the first and second legs defining a respective hole sized and configured to receive a connection feature of another surgical guide.

6. The surgical guide of claim 5, wherein at least one of the first and second legs includes at least one step, the at least one step providing a visual indication as to a location of a surface of a prosthesis to be implanted.

7. The surgical guide of claim 6, wherein the first and second legs include a plurality of steps.

8. The surgical guide of claim 5, wherein the first and second legs include a beveled surface.

9. The surgical guide of claim 1, wherein the first anatomic plane is a sagittal plane.

10. The surgical guide of claim 1, wherein the first anatomic plane is a frontal plane.

11. The surgical guide of claim 1, wherein the at least one hole includes a first hole, a second hole, and a third hole disposed between the first hole and the second hole.

12. The surgical guide of claim 11, wherein first hole is defined by a first bushing that extends from the body, the second hole is defined by a second bushing that extends from the body, and the third hole is defined by a third bushing that extends from the body.

13. The surgical guide of claim 1, wherein the body defines at least one slot that is sized and configured to receive at least one of a depth-indicating tool or a blade of a cutting tool.

14. The surgical guide of claim 1, wherein at least one of a posterior side or an anterior side of the body includes a notch configured to provide a visual indication of a location of at least one surface of a prosthesis to be implanted when the surgical guide is viewed in a sagittal plane.

15. The surgical guide of claim 1, wherein the body includes a joint line indicator.

16. The surgical guide of claim 15, wherein the joint line indicator includes at least one projection extending into the first opening defined by the body.

17. The surgical guide of claim 16, wherein the joint line indicator includes a notch formed in at least one of a posterior side or an anterior side of the body.

18. A surgical guide, comprising:

a body having a shape that corresponds to a shape of an implant to be implanted, the body defining a first opening and at least one hole that is sized and configured to receive a tool therein; and a first alignment feature coupled to at least one side of the body and configured to facilitate alignment of the surgical guide with a first anatomic plane, wherein the first alignment feature includes a second opening and a projection that terminates in a shape that is complementary to a shape of the second opening.

19. The surgical guide of claim 18, wherein the projection is located at a terminal end of a flange that has a cross-sectional geometry to facilitate coupling of the surgical guide to another surgical tool.

20. A system, comprising:

a first guide including:

a first guide body having a first side, a second side, a third side, and a fourth side, the third and fourth sides extending between the first and second sides, wherein the body defines a first opening between the first side, the second side, the third side, and the fourth side, the body further defining a first hole and a second hole each sized and configured to receive at least one of a fixation device or a cutting tool, a first alignment feature extends from the body and is configured to facilitate alignment of the first guide with a first anatomic plane, and a second alignment feature extends from the body and is configured to facilitate alignment of the first guide with a second anatomic plane that is different from the first anatomic plane; wherein the first alignment feature includes a first component and a second component, the first component defining an opening and the second component including a projection that terminates in a shape that is complementary to a shape of the opening defined in the first component.

21. The system of claim 20, wherein the first guide includes first and second legs extending from the first side of the first guide body, wherein a gap is defined between the first leg, the second leg, and the first side of the first guide body.

22. The system of claim 21, further comprising:

a second guide, the second guide having a transverse beam that extends between a first arm and a second arm, wherein the second guide is configured to be coupled to the first guide.

23. The system of claim 22, wherein first and second protrusions extend from the transverse beam of the second guide, the first and second protrusions sized and configured to be received in respective connection features defined by the first and second legs of the first guide body for coupling the second guide to the first guide.

24. The system of claim 22, wherein each of the first and second arms of the second guide define at least one connection feature for receiving an elongate radiopaque device therein.

25. The system of claim 20, further comprising:

a drill bit extending from a first end to a second end, the first end configured to be coupled to a driving tool, and the second end including at least one cutting surface, the drill bit further including at least one indicia located along a length of the drill bit at a distance from the second end corresponding to a length of an implant, wherein drill bit is sized and configured to be received within a third hole defined by the first guide body.

26. The system of claim 25, wherein the third hole defined by the first guide body is located between the first hole and the second hole.

27. The system of claim 25, wherein the at least one indicia includes a plurality of indicia, and wherein each indicia of the plurality of indicia is disposed at a respective distance from the second end of the drill bit corresponding to a length of a respective implant.

* * * * *